United States Patent
Li et al.

(10) Patent No.: US 11,046,741 B2
(45) Date of Patent: Jun. 29, 2021

(54) HUMAN NEUREGULIN-1 (NRG-1) RECOMBINANT FUSION PROTEIN COMPOSITIONS AND METHODS OF USE THEREOF

(71) Applicants: Salubris Biotherapeutics, Inc., Gaithersburg, MD (US); Genekey Biotech (Chengdu) Co., Ltd., Chengdu (CN)

(72) Inventors: John Li, Reston, VA (US); Shengwei Li, Chengdu (CN); Dixiang Luo, Chengdu (CN); Yiran Wu, Chengdu (CN); Ming Zhou, Shandong (CN); Xiaolei Zhuang, North Potomac, MD (US); Liang Hua, Zigong (CN); Pengyi Luo, Chengdu (CN); Yang Wang, Sichuan (CN)

(73) Assignees: Salubris Biotherapeutics, Inc., Gaithersburg, MD (US); Salubris (Chengdu) Biotech Co., Ltd., Chengdu (CN)

( * ) Notice: Subject to any disclaimer, the term of this patent is extended or adjusted under 35 U.S.C. 154(b) by 0 days.

(21) Appl. No.: 16/381,206

(22) Filed: Apr. 11, 2019

(65) Prior Publication Data
US 2020/0010522 A1    Jan. 9, 2020

Related U.S. Application Data

(60) Provisional application No. 62/656,246, filed on Apr. 11, 2018.

(51) Int. Cl.
*C07K 14/475* (2006.01)
*C12N 15/90* (2006.01)
*A61K 38/00* (2006.01)

(52) U.S. Cl.
CPC ........ *C07K 14/4756* (2013.01); *C12N 15/907* (2013.01); *A61K 38/00* (2013.01); *C07K 2319/00* (2013.01)

(58) Field of Classification Search
CPC ............ C07K 14/4756; C07K 2319/00; C07K 16/32; C07K 16/22; C07K 16/2863; C12N 15/907; A61P 35/00; A61P 9/00
See application file for complete search history.

(56) References Cited

U.S. PATENT DOCUMENTS

| | | |
|---|---|---|
| 5,202,238 A | 4/1993 | Fell, Jr. et al. |
| 5,204,244 A | 4/1993 | Fell et al. |
| 5,464,764 A | 11/1995 | Capecchi et al. |
| 5,487,992 A | 1/1996 | Capecchi et al. |
| 5,530,109 A | 6/1996 | Goodearl et al. |
| 5,716,930 A | 2/1998 | Goodearl et al. |
| 5,834,229 A | 11/1998 | Vandlen et al. |
| 5,932,447 A | 8/1999 | Siegall |
| 10,561,709 B2 | 2/2020 | Zhou |
| 2007/0081992 A1 | 4/2007 | Pardridge et al. |
| 2009/0226435 A1* | 9/2009 | Khare .................. C07K 14/521 424/133.1 |
| 2012/0195831 A1* | 8/2012 | Zhang .................... C07K 16/32 424/1.49 |

FOREIGN PATENT DOCUMENTS

| | | |
|---|---|---|
| EP | 0 586 607 B1 | 7/2003 |
| EP | 2 555 788 B1 | 10/2017 |
| WO | WO 1997/009425 A1 | 3/1997 |
| WO | WO 2000/064400 A2 | 11/2000 |
| WO | WO 2006/017184 A2 | 2/2006 |
| WO | WO 2007/062594 A1 | 6/2007 |
| WO | WO 2015/155998 A1 | 10/2015 |

OTHER PUBLICATIONS

Wikipedia entry "Neuregulin 1", retrieved from https://en.wikipedia.org/wiki/Neuregulin_1 on Mar. 27, 2020.*
World Health Organization, "Prevention of Cardiovascular Disease Guidelines for assessment and management of cardiovascular risk", retrieved from https://www.who.int/cardiovascular_diseases/guidelines/Full%20text.pdf on Feb. 10, 2021.*
Alimandi, et al. "Cooperative Signaling of ErbB3 and EibB2 in neoplastic transformation and human mammary carcinomas," *Oncogene* (1995), 10: p. 1813-1821.
Altschul, et al. "Basic Local Alignment Search Tool," *J. Mol. Biol.* (1990), 215: p. 403-410.
Altschul et al. "Gapped BLAST and PSI-BLAST: a new generation of protein database search programs," *Nucleic Acids Res.* (1997) 25: p. 3389-3402.
Alvarado, et al. "ErbB activation signatures as potential biomarkers for anti-ErbB3 treatment in HNSCC," PLoS One (2017), 12 (7): e0181356, 23 pages.
Barnes, et al. "Characterization of the Stability of Recombinant Protein Production in the GS-NS0 Expression System," *Biotech. Bioeng.* (2001), 73: p. 261-270.
Barnes, et al. "Advances in animal cell recombinant protein production: GS-NS0 expression system," *Cytotechnology* (2000), 32: p. 109-123.
Bellinger, et al. "Cardio-Oncology: How New Targeted Cancer Therapies and Precision Medicine Can inform Cardiovascular Discovery," *Circulation* (2015), 132: p. 2248-2258.

(Continued)

*Primary Examiner* — Gregory S Emch
(74) *Attorney, Agent, or Firm* — Cooley LLP; Matthew Pavao; Jessica D. Cande

(57) ABSTRACT

The present invention relates to a recombinant fusion protein comprising a fragment of the cardioprotective protein neuregulin-1 (NRG-1) fused to a monoclonal antibody (mAb) backbone and to a method of treating a disease or condition in a subject in need thereof comprising administering a therapeutically effective amount of the recombinant fusion protein or the pharmaceutical composition comprising the recombinant fusion protein disclosed herein.

38 Claims, 13 Drawing Sheets
Specification includes a Sequence Listing.

(56) References Cited

OTHER PUBLICATIONS

Benson, et al. "Genetics of Hypoplastic Left Heart Syndrome," *The Journal of Pediatrics* (2016), 173: p. 25-31.
Berardi, R. et al. "State of the art for cardiotoxicity due to chemotherapy and to targeted therapies: A literature review," *Critical reviews in Oncology/Hematology* (2013), 88: p. 75-86.
Bishopric, N. R. "A Growth Tonic for Heart Failure?" *JACC: Basic to Translational Science* (2016), 1 (7): p. 587-9.
Boerner, et al. "Production of antigen-specific human monoclonal antibodies from in vitro-primed human splenocytes," *J. Immunol.* (1991), 147: p. 86-95.
Booth, et al. "The use of 'universal' yeast expression vector to produce an antigenic protein of Mycobacterium leprae," *Immunol. Lett.* (1988), 19: p. 65-69.
Bruggemann, et al. "Designer Mice: The Production of Human Antibody Repertoires in Transgenic Animals," *Year Immunol.* (1993), 7: p. 33-40.
Bryant, et al. "Cardioprotection against the toxic effects of anthracyclines given to children with cancer: a systematic review," *Health Technology Assessment* (2007), 11 (27): p. 1-4.
Carraway, et al. "Neuregulin-2, a new ligand of ErbB3/ErbB4-receptor tyrosine kinases," *Nature* (1997) 387: p. 512-516.
Carter, et al. "Humanization of anti-p185HER2 antibody for human cancer therapy," *Proc. Natl. Sci. USA* (1992) 89: p. 4285-4289.
Cervellini, et al. "Sustained "MAPK/ERK" Activation in Adult Schwann Cells Impairs Nerve Repair," *The Journal of Neuroscience* (2018), 38 (3): p. 679-90.
Cespedes, et al. "Neuregulin in Heath and Disease," *Int. J. Brain Disord. Treat.* (2018), 4 (1), doi:10.23937/2469-5866/1410024; 24 pages.
Chang, et al. "Ligands for ErbB-family receptors encoded by a neuregulin-like gene," *Nature* (1997), 387: p. 509-512.
Cole, et al. "The EBV-Hybridoma Technique and its Application to Human Lung Cancer," *Monoclonal Antibodies and Cancer Therapy* (1985), Alan R. Liss, Inc.; New York; Reisfeld and Sell, editors: p. 77-96.
Dominguez, et al. "Antibody-mediated stabilization of NRG1 induces behavioral and electrophysiological alterations in adult mice," *Scientific Reports* (2018), 8: 8239; 13 pages.
Durocher, et al. "High-level and high-throughput recombinant protein production by transient transfection of suspension-growing human 293-EBNA1 cells," *Nucl. Acids. Res.* (2002), 30(2): e9; 9 pages.
Eschenhagen, et al. "Cardiovascular side effects of cancer therapies: a position statement from the Heart Failure Association of the European Society of Cardiology," *European Journal of Heart Failure* (2011), 13: p. 1-10.
Fang, et al. "Inhibition of endoplasmic reticulum stress by neuregulin-1 protects against myocardial ischemialreperfusion injury," *Peptides* (2017), 88: p. 196-207.
Farkas, et al. "Neuregulin-1 signaling is essential for nerve-dependent axolotl limb regeneration," *Development* (2016), 143: p. 2724-2731.
Favreau-Lessard, et al. "Novel Biological Therapies Targeting Heart Failure: Myocardial Rejuvenation," *Heart Fail. Clin.* (2016), 12 (3): p. 461-71, 14 pages.
Florescu, et al. "Chemotherapy-induced Cardiotoxicity," *MAEDICA—a Journal of Clinical Medicine* (2013), 8 (1): p. 59-67.
Florido, et al. "Cardiotoxicity From Human Epidermal Growth Factor Receptor-2 (HER2) Targeted.Therapies," *Journal of the American Heart Association* (2017) 6(9): pii: e006915; 14 pages provided.
Galindo, et al. "Anti-Remodeling and Anti-Fibrotic Effects of Neuregulin-1β Glial Growth Factor 2 in a Large Animal Model of Heart Failure," *Journal of the American Heart Association* (2014) 3:. e000773; 22 pages.

Ganapathy, et al. "Neuregulin-1 Administration Protocols Sufficient for Stimulating Cardiac Regeneration in Young Mice Do Not Induce Somatic, Organ, or Neoplastic Growth," *PLoS One* (2016), 11(5): e0155456; 20 pages.
Gao, et al. "A Phase II, Randomized, Double-Blind, Multicenter, Based on Standard Therapy, Placebo-Controlled Study of the Efficacy and Safety of Recombinant Human Neuregulin-1 in Patients with Chronic Heart Failure," *Journal of the American College of Cardiology* (2010), 55 (18): p. 1907-14.
Gardella, et al. "Expression of Human Parathyroid Hormone—(1-84) in *Escherichia coli* as a Factor X-cleavable Fusion Protein," *J. Biol. Chem.* (1990), 265 (26): p. 15854-15859.
Geisse, et al. "Eukaryotic Expression Systems: A Comparison," *Protein Expr. Purif.* (1996), 8: p. 271-282.
Ghigo, et al. "New signal transduction paradigms in anthracycline-induced cardiotoxicity," *Biochimica et Biophysica Acta* (2016), 1863: p. 1916-25.
Gilboa, et al. "Transfer and Expression of Cloned Genes Using Retroviral Vectors," *Biotechniques* (1986), 4 (6): p. 504-512.
Groarke, J.D. and Nohria, A. "Anthracycline Cardiotoxicity: A New Paradigm for an Old Classic," *Circulation* (2015), 131: p. 1946-9.
Hanchard, et al. "A genome-wide association study of congenital cardiovascular left-sided lesions shows association with a locus on chromosome 20," *Human Molecular Genetics* (2016), 25 (11): p. 2331-41.
Harvey, et al. "Cardiac Regeneration Therapies—Targeting Neuregulin 1 Signalling," *Heart, Lung and Circulation* (2016) 25: p. 4-7.
Hellyer, et al. "Heregulin-dependent Activation of Phosphinositide 3-Kinase and Akt via the ErbB2/ErbB3 Co-receptor," *J. Biol. Chem.* (2001), 276: p. 42153-42161.
Higashiyama, et al. "A Novel Brain-Derived Member of the Epidermal Growth Factor Family That Interacts with ErbB3 and ErbB4," *J. Biochem.* (1997), 122: p. 675-680.
Higgins, et al. "Using CLUSTAL for Multiple Sequence Alignments," Methods Enzymol. (1996), 266: p. 383-402.
Hijazi, et al. "NRG-3 in human breast cancers: Activation of multiple erbB family proteins," *Int. J. Oncol.* (1998),13: p. 1061-1067.
Hill, et al. "Intravenous Glial Growth Factor 2 (GGF2) Isoform of Neuregulin-1β Improves Left Ventricular Function, Gene and Protein Expression in Rats after Myocardial Infarction," *PLoS One* (2013), 8(2): e55741; 17 pages.
Holmes, et al. "Identification of Heregulin, a Specific Activator of p185erbB2," *Science* (1992), 256: p. 1205-1210.
Hoogenboom, H.R. and Winter, G. "By-passing Immunisation Human Antibodies from Synthetic Repertoires of Germline VH Gene Segments Rearranged in Vitro," *J. Mol. Biol.* (1992), 227: p. 381-388.
Huang, et al. "Species-Specific Effects of Neuregulin-1β (Cimaglermin alfa) on Glucose Handling in Animal Models and Humans with Heart Failure," *Toxicol. Appl. Pharmacol.* (2017) 332: 92-99, 23 pages provided.
Huston, et al. "Protein Engineering of Single-Chain Fv Analogs and Fusion Proteins," *Methods in Enzymol.* (1991), 203: p. 46-88.
Iaci, et al. "An optimized Dosing Regimen of Cimaglermin (Neuregulin 1β3, Glial Growth Factor 2) Enhances Molecular Markers of Neuroplasticity and Functional Recovery After Permanent Ischemic Stroke in Rats," *Journal of Neuroscience Research* (2016), 94: p. 253-265.
Jabbour, et al. "Parenteral administration of recombinant human neuregulin-1 to patients with stable chronic heart failure produces favourable acute and chronic haemodynamic responses," *European Journal of Heart Failure* (2011), 13: p. 83-92.
Jabbour, et al. Online Supplement Tables; "Parenteral administration of recombinant human neuregulin-1 to patients with stable chronic heart failure produces favourable acute and chronic haemodynamic responses," *European Journal of Heart Failure* (2011), 13: p. 83-92, 2 pages.
Jacobi, et al. "ErbB Family Signalling: A Paradigm for Oncogene Addiction and Personalized Oncology," *Cancers* (2017), 9 (33): doi:10.3390/cancers9040033; 24 pages.

(56) References Cited

OTHER PUBLICATIONS

Jakobovits, et al. "Germ-line transmission and expression of human-derived yeast artifical chromosome," *Nature* (1993), 362: p. 255-258.

Jakobovits, et al, "Analysis of homozygous mutant chimeric mice: Deletion of the immunoglobulin heavy-chain joining region blocks B-cell development and antibody production," *Proc. Natl. Acad. Sci. USA* (1993), 90: p. 2551-2555.

Karlin, S. and Altschul, S. F. "Methods for assessing the statistical significance of molecular sequence features by using general scoring schemes," *Proc. Natl. Acad. Sci. USA* (1990), 87: p. 2264-2268.

Karlin, S. and Altschul, S. F. "Application and statistics for multiple high-scoring segments in molecular sequences," *Proc. Natl. Acad. Sci. USA* (1993), 90: p. 5873-5877.

Kaufman, R.J. "Overview of Vector Design for Mammalian Gene Expression," *Mol. Biotechnol.*(2000), 16: p. 151-160.

Kraus, et al. "Isolation and characterization of ERBB3, a third member of the ERBB / epidermal growth factor receptor family: Evidence for overexpression in a subset of human mammary tumors," *Proc. Natl. Acad. Sci. USA* (1989), 86: p. 9193-9197.

Kraus, et al. "Demonstration of ligand-dependent signaling by the erbB-3 tyrosine kinase and its constitutive activation in human breast tumor cells," *Proc. Natl. Acad. Sci. USA* (1993), 90: p. 2900-2904.

Lasiene, et al. "Neuregulin 1 confers neuroprotection in SOD1-linked amyotrophic lateral sclerosis mice via restoration of C-boutons of spinal motor neurons," *Acta Neuropathologica Communications* (2016), 4(15): doi 10.1186/s40478-016-0286-7; 13 pages.

Lefranc, M.P. Appendix 1P; "Nomenclature of the Human Immunoglobulin Genes," *Current Protocols in Immunology* (2000), Supp. 40: p. A1P.1-A.1P.37.

Lenihan, et al. "A Phase I, Single Ascending Dose Study of Cimaglermin Alfa (Neuregulin 1β3) in Patients with Systolic Dysfunction and Heart Failure," *JACC: Basic to Translational Science* (2016), 1 (7): p. 576-86.

Lenneman, C. G. "Neuregulin-1 Signaling in the Pathogenesis of Chemotherapy-Induced Heart Failure," *Current Heart Failure Reports* (2014), 11 (2): 134-138; 14 pages provided.

Lin, Z. and Pu, W. T. "Strategies for cardiac regeneration and repair," *Sci. Transl. Med.* (2014), 6 (239): 239ry 1; 23 pages.

Longo, et al. "Refining Liver Safety Risk Assessment: Application of Mechanistic Modeling and Serum Biomarkers to Cimaglermin Alfa (GGF2) Clinical Trials," *Clinical Pharmacology & Therapeutics* (2017), 102 (6): p. 961-9.

LoRusso, et al. "Phase 1 Study of U3-1287, a Fully Human Anti-HER3 Monoclonal Antibody, in Patients with Advanced Solid Tumors," *Clinical Cancer Research* (2013), 19 (11): p. 3078-3087.

Lyu, et al. "Understanding the biology of HER3 receptor as a therapeutic target in human cancer," *Acta Pharmaceutica Sinica B* (2018), 8 (4): p. 503-10.

Makrides, S.C. "Components of Vectors for Gene Transfer and Expression in Mammalian Cells," *Protein Expr. Purif* (1999), 17: p. 183-202.

Marks, et al. "By-passing Immunization Human Antibodies from V-gene Libraries Displayed on Phage," *J. Mol. Biol.* (1991), 222: p. 581-597.

McBride, et al. "Association of Common Variants in ERBB4 with Congenital Left Ventricular Outflow Tract Obstruction Defects," *Birth Defects Res. A. Clin. Mol. Teratol.* (2011), 91 (3): 162-168; 14 pages provided.

McElroy, et al. "The ErbB4 Ligand Neuregulin-4 Protects against Experimental Necrotizing Enterocolitis," *The American Journal of Pathology* (2014), 184 (10): p. 2768-78.

McGowan, et al. "Anthracycline Chemotherapy and Cardiotoxicity," *Cardiovasc. Drugs Ther.* (2017), 31: p. 63-75.

Morano, et al. "Modulation of the Neuregulin 1/ErbB system after skeletal muscle denervation and reinnervation," *Scientific Reports* (2018), 8(5047): doi 10.1038/s41598-018-23454-8; 13 pages.

Morrison, et al. "Chimeric human antibody molecules: Mouse antigen-binding domains with human constant region domains," *Proc. Natl. Acad Sci. USA* (1984), 81: p. 6851-6855.

Neuberger, et al. "A hapten-specific chimaeric IgE antibody with human physiological effector function," *Nature* (1985), 314: p. 268-270.

Norderhaug, et al. "Versatile vectors for transient and stable expression of recombinant antibody molecules in mammalian cells," *J. Immunol. Methods* (1997), 204: p. 77-87.

Odiete, et al. "Neuregulin in Cardiovascular Development and Disease," *Circ. Res.* (2012), 111: p. 1376-1385.

Orlandi, et al. "Cloning immunoglobulin variable domains for expression by the polymerase chain reaction," *Proc. Natl. Acad. Sci. USA* (1989), 86: p. 3833-3837.

Parodi, E. M. and Kuhn, B. "Signalling between microvascular endothelium and cardiomyocytes through neuregulin," *Cardiovascular Research* (2014), 102: p. 194-204.

Parry, et al. "Effects of neuregulin GGF2 (cimaglermin alfa) dose and treatment frequency on left ventricular function in rats following myocardial infarction," *European Journal of Pharmacology* (2017) 796: p. 76-89.

Pearson, W. R. and Lipman, D. J. "Improved tools for biological sequence comparison," *Proc. Natl. Acad. Sci. USA* (1988), 85: p. 2444-8.

Pentassuglia, et al. "Neuregulin-1β promotes glucose uptake via PI3K/Akt in neonatal rat cardiomyocytes," *Am. J. Physiol. Endocrinol. Metab.* (2016), 310: p. E782-94.

Piotrowska, et al. "Early transcriptional alteration of histone deacetylases in a murine model of doxorubicin-induced cardiomyopathy," *PLoS One* (2017), 12(6): e0180571, 12 pages.

Plowman, et al. "Molecular cloning and expression of an additional epidermal growth factor receptor-related gene," *Proc. Natl. Acad. Sci. USA* (1990), 87: p. 4905-4909.

Prescott, et al. "Evaluation of Therapeutics for Advanced-Stage Heart Failure and Other Severly-Debilitating or Life-Threatening Diseases," *Clinical Pharmacology & Therapeutics* (2017), 102 (2): p. 219-27.

Riechmann, et al. "Reshaping human antibodies for therapy," *Nature* (1988), 332: p. 323-327.

Rupert, C. E. and Coulombe K.L.K. "The Roles of Neuregulin-1 in Cardiac Development, Homeostasis, and Disease," *Biomarker Insights* (2015), 10 (S1): p. 1-9.

Santoro, F. and Sahara, M. "A specified therapeutic window for neuregulin-1 to regenerate neonatal heart muscle," *Ann. Transl. Med.* (2015), 3(17): 249, 6 pages.

Schlaeger, E.-J. and Chrisiensen, K. "Transient gene expression in mammalian cells grown in serum-free suspension culture," *Cytotechnology* (1999), 30: p. 71-83.

Schlaeger, E.-J. "The protein hydrolysate, Primatone RL, is a cost-effective multiple growth promoter of mammalian cell culture in serum-containing and serum-free media and displays anti-apoptosis properties," *J. Immunol. Methods* (1996), 194: p. 191-199.

Shimizu, et al. "Phase 1 study of new formulation of patritumab (U3-1287) Process 2, a fully human anti-HER3 monoclonal antibody in combination with erlotinib in Japanese patients with advanced non-small cell lung cancer," *Cancer Chemother. Pharmacol.* (2017), 79: p. 489-95.

Shimizu, et al. Supplementary Material to; "Phase 1 study of new formulation of patritumab (U3-1287) Process 2, a fully human anti-HER3 monoclonal antibody in combination with erlotinib in Japanese patients with advanced non-small cell lung cancer," *Cancer Chemother. Pharmacol.* (2017), 79: 4 pages.

Shoop, et al. "Glial Growth Factor 2 Regulates Glucose Transport in Healthy Cardiac Myocytes and During Myocardial Infarction via an Akt-Dependent Pathway," *Frontiers in Physiology* (2019), 10: 189; doi 10.3389/fphys.2019.00189, 13 pages.

Sliwkowski, et al. "Coexpression of erbB2 and erbB3 Proteins Reconstitutes a High Affinity Receptor for Heregulin," *J. Biol. Chem.* (1994), 269 (20): p. 14661-14665.

Steinkamp, et al. "erbB3 Is an Active Tryosine Kinase Capable of Homo- and Heterointeractions," *Molecular and Cellular Biology* (2014), 34 (6): p. 965-77.

(56) References Cited

OTHER PUBLICATIONS

Studier, et al. "Use of T7 RNA Polymerase to Direct Expression of Cloned Genes," *Methods in Enzymol.* (1990), 185: p. 60-89.
Takahashi, et al. "ERBB4 Mutations that Disrupt the Neuregulin-ErbB4 Pathway Cause Amyotrophic Lateral Sclerosis Type 19," *The American Journal of Human Genetics* (2013), 93: p. 900-5.
Torelli, A. and Robotti, C. A. "Advance and Adam: two algorithms for the analysis of global similarity between homologous informational sequences," *Comput. Appl. Biosci.* (1994),10 (1): p. 3-6.
Van Dijk, M.A. and Van De Winkel, J.G. "Human antibodies as next generation therapeutics," *Curr. Opin. Chem. Biol.* (2001), 5: p. 368-374.
Vandekerckhove, et al. "Neuregulin-1 attenuates development of nephropathy in a type 1 diabetes mouse model with high cardiovascular risk," *Am. J. Physiol. Endocrinol. Metab.* (2016), 310: p. E495-504.
Vermeulen, et al. "ErbB2 signaling at the crossing between heart failure and cancer," *Basic Res. Cardiol.* (2016), 111: 60, 14 pages.
Wakui, et al. "Phase 1 and dose-finding study of patritumab (U3-1287), a human monoclonal antibody targeting HER3, in Japanese patients with advanced solid tumors," *Cancer Chemother. Pharmacol.* (2014) 73: p. 511-16.
Wang, et al. "Evaluation of neuregulin-1's neuroprotection against ischemic injury in rats using diffusion tensor imaging," *Magnetic Resonance Imaging* (2018), 53: p. 63-70.
Watson, et al. "Molecular Biology of the Gene," *The Benjamin/Cummings Pub. co.* (1987) 4th ed., Chapter 8, pp. 214-238.
Werner, et al. "Appropriate Mammalian Expression Systems for Biopharmaceuticals," *Arzneitmittelforschung* (1998), 48: p. 870-880.
Wu, et al. "Neuregulin-1 and Neurovascular Protection," in Brain Neurotrauma: Molecular, Neuropsychological, and Rehabilitation Aspects. CRC Press/Taylor & Francis; Boca Raton, FL (2015); Chapter 39; downloaded from NCBI Bookshelf, 10 pages.
Zensun. "Fact Sheets: Neucardin: a Novel First in Class Therapy to Treat Chronic Heart Failure." *Zenzun USA, Inc.*, 2 pages.
Zhou, et al. "Recombinant human neuregulin-1β is protective against radiation-induced myocardial cell injury," *Molecular Medicine Reports* (2016), 14: p. 325-330.
Zhou, et al. "Regulation of the NRG1/ErbB4 Pathway in the Intrinsic Cardiac Nervous System Is a Potential Treatment for Atrial Fibrillation," *Frontiers in Physiology* (2018), 9: 1082; 9 pages.
Conceicao, et al. "Animal models of heart failure with preserved ejection fraction." Neth Heart J. 2016;24(4):275-286.
Haq, et al. "Heart failure with preserved ejection fraction—unwinding the diagnosis mystique." Am J Cardiovasc Dis. 2014;4(3):100-113.
Ho, et al. "Differential Clinical Profiles, Exercise Responses, and Outcomes Associated With Existing HFpEF Definitions." Circulation. 2019;140(5):353-365.
Hummel, et al. "Echocardiographic estimation of left ventricular and pulmonary pressures in patients with heart failure and preserved ejection fraction: a study utilizing simultaneous echocardiography and invasive measurements." Eur J Heart Fail. 2017;19(12):1651-1660.
Li, et al. "Gene transfer of human neuregulin-1 attenuates ventricular remodeling in diabetic cardiomyopathy rats." Exp Ther Med. 2013;6(5):1105-1112.
Liu, et al. "Neuregulin-1/erbB-activation improves cardiac function and survival in models of ischemic, dilated, and viral cardiomyopathy." J Am Coll Cardiol. 2006;48(7):1438-1447.
Parodi and Kuhn. "Signaling between microvascular endothelium and cardiomyocytes through neuregulin." Cardiovascular Research 2014: 102: 194-204.
Pfeffer, et al. "Heart Failure With Preserved Ejection Fraction in Perspective." Circ Res. 2019;124(11):1598-1617.
Pieske, et al. "How to diagnose heart failure with preserved ejection fraction: the HFA-PEFF diagnostic algorithm: a consensus recommendation from the Heart Failure Association (HFA) of the European Society of Cardiology (ESC)." Eur Heart J. 2019;40(40):3297-3317.
Tschope, et al. "The role of NT-proBNP in the diagnostics of isolated correlation with echocardiographic and invasive measurements." Eur Heart diastolic dysfunction: J. 2005;26(21):2277-2284.
Hervent, et al. "Neuregulin-1 antagonizes myocardial fibrosis and diastolic dysfunction in angiotensin-II treated mice." *European Heart Journal*, vol. 34, Issue suppl. 1, Aug. 2013, P2434, https://doi.org/10.1093/eurheartj/eht308.P2434.

* cited by examiner

Molecular Schematic of Anti-HER3 mAb/NRG-1 Fusion Protein

SDS-PAGE Analysis of Anti-HER3 mAb/NRG-1 Fusion Protein

Lane 1: Prestained Protein Ladder
Lane 2: Anti-HER3 mAb/NRG-1 Fusion Protein
Lane 3: Anti-HER3 mAb/NRG-1 Fusion Protein (without Fc mutations)
Lane 4: anti-HER3 mAb

HUMAN NEUREGULIN-1 (NRG-1) RECOMBINANT FUSION PROTEIN COMPOSITIONS AND METHODS OF USE THEREOF

CROSS REFERENCE TO RELATED APPLICATIONS

This application claims priority to, and the benefit of, U.S. Provisional Application No. 62/656,246, filed on Apr. 11, 2018, the contents of which are incorporated herein by reference in their entirety.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Mar. 16, 2019, is named SBTI-001-001US_SeqList.txt and is 31,328 bytes in size.

BACKGROUND OF THE INVENTION

Neuregulin (NRG; heregulin, HRG), also known as glial growth factor (GGF) and new differentiation factor (NDF), is a type of glycoprotein with a molecular weight of 44 KD. The NRG protein family has four members: NRG-1, NRG-2, NRG-3 and NRG-4. NRG (including NRG-1) plays a particularly important role in the development of the heart. As a ligand of tyrosine kinase receptors of the ErbB family, NRG-1 directly binds to membrane-bound ErbB3 or ErbB4, inducing dimerization to create ErbB2/ErbB4, ErbB2/ErbB3, ErbB3/ErbB3 and ErbB4/ErbB4 complexes, and subsequent intracellular signaling. In animal models, expression of NRG induces paracrine signaling to promote growth and differentiation in cardiac tissue during embryogenesis, with deletion of any of ErbB2, ErbB4 or NRG-1 leading to embryonic lethality. Further, cancer therapies blocking ErbB2 receptor signaling have been shown to have significant cardiotoxicity side-effects, demonstrating in humans that ErbB2-mediated signaling is essential not only for development but also for the homeostasis of healthy cardiac tissue.

Evidence also shows that NRG-1 signal transduction plays a part in the development and function of other organ systems, as well as in the pathogenesis of human disease (including schizophrenia and head and neck cancer). NRG-1 has many isomers. Research in gene mutated mice (gene knock-out mice) indicates that isomers with different N terminal regions or EGF-like domains have different in vivo functions. The present invention is based on the NRG-1βa2 isoform.

Endogenous NRG-1 binds to and induces signaling through both ErbB3 (HER3) and ErbB4 (HER4). Numerous pre-clinical and clinical studies have shown the therapeutic potential of NRG-1 across a variety of cardiovascular indications, principally through its interactions with cardiomyocyte-expressed ErbB4 (HER4). However, three key factors limit the clinical applications and utility of recombinant human NRG-1 (rhNRG-1). First, signaling of NRG-1 through HER3 may promote cancer development and/or progression, raising significant concerns for any application requiring chronic administration or without grave cardiovascular (CV) risk factors. Second, over-activation of HER3 by NRG-1 may disrupt gastrointestinal (GI) epithelial integrity and homeostasis, leading to severe GI toxicity and thus loss of therapeutic window for NRG-1. Third, both clinical-stage active protein fragments of rhNRG-1 have shown a short half-life, indicating that burdensome dosing and administration schedules may be required to achieve the desired therapeutic levels of exposure. Hence, there exists a need to provide an NRG-1-based therapeutic which retains clinically significant therapeutic potential across a variety of cardiovascular indications, but with lower risk of oncogenesis or promotion of cancer progression, better GI tolerability, and a more favorable pharmacokinetic (PK) profile.

The present invention addresses these needs by providing a recombinant protein comprising a fusion of the rhNRG-1 active domain with a HER3-specific antagonist antibody: HER3 signaling is blocked in a way that mitigates the oncogenic risk and GI toxicity of rhNRG-1, and at the same time the antibody backbone format confers a molecular half-life of a typical monoclonal antibody, enabling more convenient dosing and administration for the product.

SUMMARY OF THE INVENTION

In one aspect, the present invention relates to a recombinant fusion protein comprising a fragment of the cardioprotective protein neuregulin-1 (NRG-1) fused to a monoclonal antibody (mAb) backbone. In a related aspect, the NRG-1 fragment is fused to the C-terminus of the antibody heavy chain via a linker. In another related aspect, NRG-1 is attached to the linker via the first ($1^{st}$) amino acid on the N-terminus of NRG-1, which in one embodiment is a Serine (S or Ser) amino acid. In a related aspect, the fragment is an active fragment that comprises the active domain of NRG-1. In another related aspect the mAb is monospecific for ErbB3 (HER3). In another related aspect, the NRG-1 is the NRG-1 β2a isoform.

In another aspect, the invention relates to a pharmaceutical composition comprising a recombinant fusion protein comprising a fragment of the cardioprotective protein neuregulin-1 (NRG-1) fused to an anti-HER3 monoclonal antibody backbone and a pharmaceutically acceptable carrier, diluent or excipient.

In another aspect, the invention relates to a method of treating a disease or condition in a subject in need thereof, the method comprising administering a therapeutically effective amount of the recombinant fusion protein or the pharmaceutical composition comprising the recombinant fusion protein disclosed herein.

In another aspect, the invention relates to a method of preventing, inhibiting, suppressing or delaying the onset of a cardiovascular disease or condition in a subject, the method comprising administering an effective amount of the recombinant fusion protein disclosed herein.

In another aspect, the invention relates to a method of treating a CNS-related disease or condition in a subject in need thereof, the method comprising administering a therapeutically effective amount of the recombinant fusion protein.

In another aspect, the invention relates to a method of preventing, inhibiting, suppressing or delaying the onset of a CNS-related disease or condition in a subject, the method comprising administering an effective amount of the recombinant fusion protein.

In another related aspect, the NRG-1 binds to and induces signaling through ErbB4 (HER4). In another related aspect, the mAb inhibits NRG-1 signaling through ErbB3 (HER3).

In another aspect, the invention relates to a kit comprising an effective amount of a recombinant fusion protein of the invention or pharmaceutical composition comprising a recombinant fusion protein of the invention.

Other features and advantages of the present invention will become apparent from the following detailed description examples and figures. It should be understood, however, that the detailed description and the specific examples while indicating embodiments of the invention are given by way of illustration only, since various changes and modifications within the spirit and scope of the invention will become apparent to those skilled in the art from this detailed description.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawing wherein:

FIG. 2A illustrates a molecular schematic of an anti-HER3 mAb/NRG-1 fusion protein of the disclosure. FIG. 2B shows representative data generated by SDS-PAGE analysis. FIG. 2C shows Western blot results detected by primary antibody specific for the 61-amino acid active fragment of NRG-1 comprising the HER3/4 binding domain ("NRG-1", R&D Systems, Minneapolis, Minn.). FIG. 2D shows Western blot results detected by primary antibody specific for IgG.

FIG. 4A shows the mean relative growth rate in the NCI-N87 gastric cancer cell line. FIG. 4B shows the mean relative growth rate in the MCF-7 breast cancer cell line. FIG. 4C shows the mean relative growth rate in the RT-112 bladder cancer cell line. FIG. 4D shows the mean relative growth rate in the T47D breast cancer cell line. Compared to the control NRG-1 peptide and GP120 mAb/NRG-1 fusion protein, the recombinant fusion protein provided herein demonstrates markedly lower activity in promoting cancer cell proliferation.

FIG. 5A is a plot showing the relative ratio of phospho-AKT (pAKT) to total AKT (tAKT) versus antibody concentration (in nM) in human cardiomyocytes treated with the recombinant fusion protein of the disclosure and controls. FIG. 5B is a Western Blot analysis of AKT phosphorylation in human cardiomyocytes treated with the recombinant fusion protein of the disclosure and controls.

FIG. 6A shows the assay principle for detecting ligand-induced dimerization. PathHunter Dimerization Assay developed by Eurofins DiscoverX (Fremont, Calif.) is used for detecting ligand-induced dimerization of two subunits of a receptor-dimer pair. β-gal enzyme is split into two fragments, ProLink (PK) and enzyme receptor (EA). The cells have been engineered to co-express target protein 1 fused to enzyme donor PK, and target protein 2 fused to enzyme acceptor EA. Binding of ligand to one target protein induces it to interact with the other target protein, forcing complementation of the two enzyme fragments and resulting in the enzyme reaction to release chemiluminescent signal which is detected as Relative Fluorescence Unit or RFU. FIG. 6B is a plot illustrating that the recombinant fusion protein provided herein can induce HER2/HER4 dimerization with potency comparable to NRG-1. FIG. 6C is a plot illustrating that the recombinant fusion protein provided herein is significantly less potent than NRG-1 in inducing HER2/HER3 dimerization. These findings further validate that the recombinant fusion protein provided herein preserves the full HER2/4 signaling potential of NRG-1 while significantly reducing HER2/3 signaling induction.

DETAILED DESCRIPTION

Figure 1:
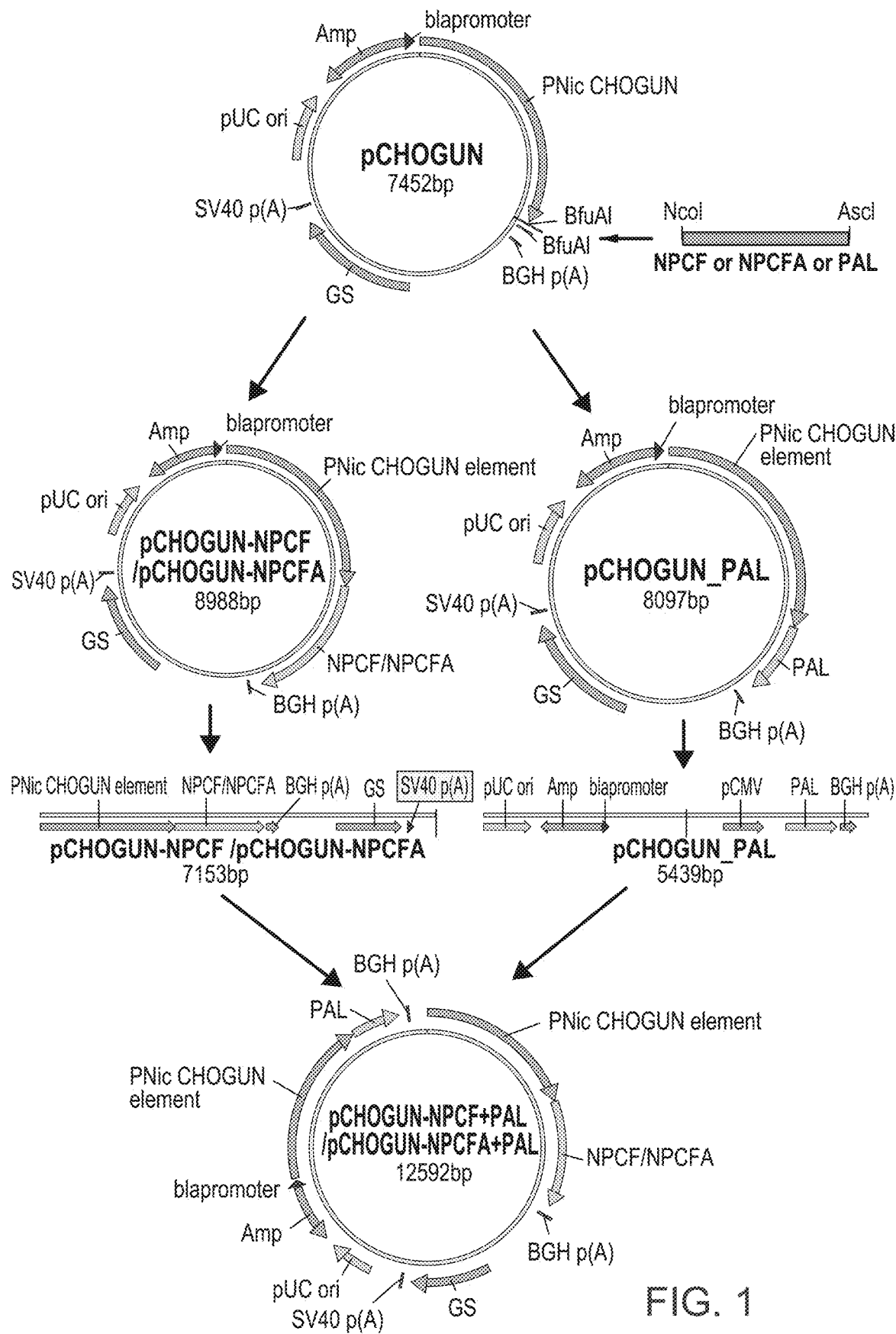
FIG. 1 shows the Construction of the expression plasmids for expressing the recombinant fusion protein disclosed herein.

The current invention utilizes a recombinant fusion protein comprising a fusion between a monoclonal antibody-fused to an active fragment of a neuregulin-1 protein isoform across a variety of cardiovascular and central nervous system (CNS) indications.

Definitions

Unless defined otherwise, technical and scientific terms used herein have the same meaning as commonly understood by one of ordinary skill in the art to which this invention belongs.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

"Neuregulin or neuregulin analogs" are molecules that can activate ErbB2/ErbB4 or ErbB2/ErbB3 heterodimer protein tyrosine kinases, such as all neuregulin isoforms, neuregulin EGF domain alone, neuregulin mutants, and any kind of neuregulin-like gene products that also activate the above receptors. The preferred "neuregulin" used in this invention is a polypeptide fragment of human neuregulin 1 β2 isoform containing the EGF-like domain and the receptor binding domain. In one embodiment, the neuregulin fragment is an active fragment. Neuregulin-1 (NRG-1) and isoforms thereof are also known in the art as neuregulin 1 (NRG1), glial growth factor (GGF), Heregulin (HGL), HRG, new differentiation factor (NDF), ARIA, GGF2, HRG1, HRGA, SMDF, MST131, MSTP131 and NRG1 intronic transcript 2 (NRG1-IT2).

The terms "ErbB3", "ErbB3 (HER3)", "HER3" refer to the same protein (or the same gene when in reference thereto) and are used interchangeably herein. In some embodiments, the recombinant fusion comprises a monoclonal antibody portion that is specific for ErbB3. ErbB3 (erb-b2 receptor tyrosine kinase 3) is also known in the art as FERLK, LCCS2, ErbB-3, c-erbB3, erbB3-S, MDA-BF-1, c-erbB-3, p180-ErbB3, p45-sErbB3 and p85-sErbB3.

In one embodiment, the terms "ErbB4", "ErbB4 (HER4)", "HER4" refer to the same protein (or the same gene when in reference thereto) and are used interchangeably herein. ErbB4 (erb-b2 receptor tyrosine kinase 4) is also known in the art as ALS19 and p180erbB4.

In one embodiment, the terms "ErbB2", "ErbB2 (HER2)", "HER2" refer to the same protein (or the same gene when in reference thereto) and are used interchangeably herein. ErbB2 (erb-b2 receptor tyrosine kinase 2) is also known in the art as NEU, NGL, TKR1, CD340, HER-2, MLN 19 and HER-2/neu.

The term "active," as used herein, refers to a fragment having a biological activity or biological function. In some embodiments, the activity is equal to or approximates the activity of the wild-type protein.

The term "subject" as used herein includes, but is not limited to, a mammal, including, e.g., a human, non-human primate (e.g., monkey), mouse, pig, cow, goat, rabbit, rat, guinea pig, hamster, horse, monkey, sheep, or other non-human mammal, a non-mammal, including, e.g., a non-mammalian vertebrate, such as a bird (e.g., a chicken or duck) or a fish; and a non-mammalian invertebrate. In some embodiments, the methods and compositions of the invention are used to treat (both prophylactically and/or therapeutically) non-human animals. The term "subject" can also refer to patients, i.e. individuals awaiting or receiving medical care.

The term "pharmaceutical composition" herein means a composition suitable for pharmaceutical use in a subject, including an animal or human. A pharmaceutical composition generally comprises an effective amount of an active agent (e.g., the recombinant fusion proteins of the invention) and a pharmaceutically acceptable carrier, diluent or excipient (e.g., a buffer, adjuvant, or the like).

The term "effective amount" means a dosage or amount sufficient to produce a desired result. The desired result may comprise an objective or subjective improvement in the recipient of the dosage or amount (e.g., long-term survival, decrease in number and/or size of tumors, effective prevention of a disease state, etc.).

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as the recombinant fusion protein of the invention, or composition thereof, that, when administered to a subject who does not display signs or symptoms of a pathology, disease or disorder (or who displays only early signs or symptoms of a pathology, disease, or disorder) diminishes, prevents, or decreases the risk of the subject developing the pathology, disease, or disorder. A "prophylactically useful" agent or compound (e.g., a recombinant fusion protein of the invention) refers to an agent or compound that is useful in diminishing, preventing, treating, or decreasing development of a pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such a recombinant fusion protein of the invention, or a composition thereof, that eliminates or diminishes signs or symptoms of a pathology, disease or disorder, when administered to a subject suffering from such signs or symptoms. A "therapeutically useful" agent or compound (e.g., a recombinant fusion protein of the invention) indicates that an agent or compound is useful in diminishing, treating, or eliminating such signs or symptoms of the pathology, disease or disorder.

The term "treating cancer" as used herein, unless otherwise indicated, means reversing, alleviating, inhibiting the progress of, or preventing, either partially or completely, the growth of tumors, tumor metastases, or other cancer-causing or neoplastic cells in a subject. The term "treatment" as used herein, unless otherwise indicated, refers to the act of treating.

The term "treating cardiovascular disease" as used herein, unless otherwise indicated, means preventing, inhibiting, suppressing, delaying, reversing, or alleviating, either partially or completely, the onset of a cardiovascular disease or condition in a subject, or the progression of a pre-existing cardiovascular disease or condition, or a symptom thereof, in a subject. Non-limiting examples of cardiovascular diseases that can be treated by the methods of the disclosure include chronic heart failure/Congestive heart failure (CHF), acute heart failure/myocardial infarction (MI), left ventricular systolic dysfunction, reperfusion injury associated with MI, chemotherapy-induced cardiotoxicity (adult or pediatric), radiation-induced cardiotoxicity, adjunct to surgical intervention in pediatric congenital heart disease. Non-limiting examples of symptoms of cardiovascular disease include shortness of breath, cough, rapid weight gain, swelling in legs, ankles and abdomen, dizziness, fatigue, weakness, dizziness, chest pain, fainting (syncope), tachychardia and bradychardia. Methods of determining the progression of cardiovascular disease and the effectiveness of treatment will be readily apparent to one of ordinary skill in the art. For example, the progression of various cardiovascular diseases can be determined by ejection fraction, electrocardiogram (ECG), Holter monitoring, echocardiogram, stress test, cardiac catheterization, cardiac computerized tomography (CT) scan and cardiac magnetic resonance imaging (MRI).

The term "treating a central nervous system (CNS)-related disease" as used herein, unless otherwise indicated, means method of preventing, inhibiting, suppressing, delaying, reversing or alleviating, either partially or completely, the onset of a CNS-related disease or condition in a subject. The term "treating a CNS-related disease" also can also mean reversing, slowing or otherwise alleviating a pre-existing CNS-related disease or condition, or a symptom thereof. Exemplary but non-limiting examples of CNS-related disease or conditions that can be treated with the methods of the disclosure include amyotrophic lateral sclerosis (ALS), Parkinson's disease, Alzheimer's Disease, Bell's Palsy, epilepsy and seizures, Guillain-Barre Syndrome, stroke, traumatic brain injury, multiple sclerosis or a combination. Treating CNS-related diseases can improve or prevent symptoms such as tremors, bradykinesia, rigid muscles, loss of balance, impaired posture, speech changes, loss of motor control, paralysis, trouble swallowing, muscle cramps, seizures, memory loss and confusion.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 90%, at least 91%, at least 92%, at least 93%, at least 94%, at least 95%, at least 96%, at least 97%, at least 98% identity, or at least 99% identity (e.g., as determined using one of the methods set forth infra).

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant (Kd) of <1 µM, <100 nM, <10 nM, <1 nM, or <0.1 nM.

In certain embodiments, an antibody specifically binds to an epitope on a protein that is conserved among the protein from different species. In another embodiment, specific binding can include, but does not require exclusive binding.

As used in this specification, the singular forms "a", "an", and "the" include plural references unless the context clearly dictates otherwise. Thus, for example, references to "neuregulin" or "a neuregulin peptide" includes mixtures of such neuregulins, neuregulin isoforms, and/or neuregulin-like polypeptides. Reference to "the formulation" or "the method" includes one or more formulations, methods, and/or steps of the type described herein and/or which will become apparent to those persons skilled in the art upon reading this disclosure.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide preferably having at least 20 contiguous or at least 50 contiguous amino acids of the polypeptide.

Unless otherwise indicated by context, a "derivative" is a polypeptide or fragment thereof having one or more non-conservative or conservative amino acid substitutions relative to a second polypeptide (also referred to as a "variant"); or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, polypeptides containing one or more analogs of an amino acid (e.g., unnatural amino acids and the like), polypeptides with unsubstituted linkages, as well as other modifications known in the art, both naturally and non-naturally occurring.

An "isolated" polypeptide is one which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. An isolated polypeptide includes an isolated antibody, or a fragment or derivative thereof.

The term "about" as used herein means in quantitative terms plus or minus 5%, or in another embodiment plus or minus 10%, or in another embodiment plus or minus 15%, or in another embodiment plus or minus 20%.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference for the purpose of disclosing and describing material for which the reference was cited in connection with.

Recombinant Fusion Protein—Antibody

The current invention utilizes a recombinant fusion protein comprising a fusion between a monoclonal antibody-fused to a fragment of a neuregulin-1 protein isoform for use across a variety of cardiovascular and neurologic indications. In typical embodiments, the antibody is specific for ERBB3 (HER3).

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the F(ab')2dimer into an Fab' monomer. The Fab' monomer is essentially an Fab with part of the hinge region (see, Fundamental Immunology, W. E. Paul, ed., Raven Press, New York (1999), for a more detailed description of other antibody fragments). While various antibody fragments are defined in terms of the digestion of an intact antibody, one of skill will appreciate that such Fab' fragments, etc. may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv or scFv) antibodies in which a variable heavy and a variable light chain are joined together (directly or through a peptide linker) to form a continuous polypeptide. Antibodies include single domain antibodies, which comprise an antibody fragment consisting of a single monomeric variable antibody domain that is able to bind selectively to an antigen domain. Exemplary single domain antibodies include VHH fragments, which were originally isolated from camelids.

The antibody domain of the fusion protein optionally comprises all or part of an immunoglobulin molecule and optionally contains all or part of an immunoglobin variable region (i.e., the area of specificity for the disease related antigen) and optionally comprises region(s) encoded by a V gene, and/or a D gene and/or a J gene.

As explained above (see, Definitions, supra) the antibodies used herein optionally comprise F(ab)2, F(ab')2, Fab, Fab', scFv, single domain antibodies, etc. depending upon the specific requirements of the embodiment. Some embodiments utilize fusion proteins comprising IgG domains. However, other embodiments comprise alternate immunoglobins such as IgM, IgA, IgD, and IgE. Furthermore, all possible isotypes of the various immunoglobins are also encompassed within the current embodiments. Thus, IgG1, IgG2, IgG3, etc. are all possible molecules in the antibody domains of the antibody-immunostimulant fusion proteins used in the invention. In addition to choice in selection of the type of immunoglobin and isotype, different embodiments of the invention comprise various hinge regions (or functional equivalents thereof). Such hinge regions provide flexibility between the different domains of the antibody-immunostimulant fusion proteins. See, e.g., Penichet, et al. 2001 "Antibody-cytokine fusion proteins for the therapy of cancer" J Immunol Methods 248:91-101.

In some embodiments, the mAb comprised by the recombinant fusion protein of the invention is monospecific for ErbB3 (HER3)).

Human HER3 (ErbB-3, ERBB3, c-erbB-3, c-erbB3, receptor tyrosine-protein kinase erbB-3) encodes a member of the epidermal growth factor receptor (EGFR) family of receptor tyrosine kinases which also includes HER1 (also known as EGFR), HER2, and HER4 (Kraus, M. H. et al, PNAS 86 (1989) 9193-9197; Plowman, G. D. et al, PNAS 87 (1990) 4905-4909; Kraus, M. H. et al, PNAS 90 (1993) 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound HER3 protein has a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N. J., J. Biol. Chem. 276 (2001) 42153-4261; Singer, E., J. Biol.

In one embodiment, the human ERBB3 protein comprises the following amino acid sequence provided in GenBank AAH02706.1 and set forth in SEQ ID NO: 1:
MRANDALQVLGLLFSLARG-
SEVGNSQAVCPGTLNGLSVTGDAENQYQTLYK
LYERCEVVMGN-
LEIVLTGHNADLSFLQWIREVTGYVLVAMNEF-
STLPLPNLRVVRG TQVYDGKFAIFVMLNYN-
TNSSHALRQLRLTQLTEILSGGVYIEKNDKLCHMDTI-
DWR DIVRDRDAEIVVKDN-
GRSCPPCHEVCKGRCWGPGSEDCQTLTKTI- CAPQCNGHCFGP NPNQCCHDECAGGCSGPQDTDC-FACRHFNDSGACVPRCPQPLVYNKLTFQLEPNPH TKYQYGGVCVASCPHNFVVDQTSCVRACPPDK-MEVDKNGLKMCEPCGGLCPKAF (SEQ ID NO: 1). It is to be understood that the ERBB3 (HER3) sequence targeted by the antibody of the present methods and compositions may be an isomer, homolog, or variant of SEQ ID NO: 1.

In one embodiment, the mAb of the recombinant fusion protein provided herein is an anti-Her3 mAb that inhibits NRG-1 signaling through ErbB3 (HER3).

In a particular embodiment, the mAb comprised by the recombinant fusion protein of the invention comprises an anti-HER3 mAb. Such anti-HER3 antibodies may include, but are not limited to the following: patritumab, seribantumab (fully human mAb), LJM716, KTN3379, AV-203, REGN1400, GSK2849330, or MM-141. Such antibodies may be also be selected from any of the following forms, including, chimeric, bi-specific, non-human, fully human, or humanized form, so long as they bind to and inhibit signaling from human ERBB3 (HER3). In some embodiments, the anti-HER3 antibody is of human origin.

In some embodiments, the term "antibody" encompasses the various forms of antibody structures including, but not being limited to, whole antibodies and antibody fragments. The antibody according to the invention is preferably a human antibody, humanized antibody, chimeric antibody, or further genetically engineered antibody as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to the respective antigen being able to assemble together with a $V_H$ domain to a functional antigen binding site and thereby providing the properties of an antibody according to the invention. The terms "monoclonal antibody" or "monoclonal antibody composition" as used herein refer to a preparation of antibody molecules of a single amino acid composition.

In some embodiments, a chimeric antibody may be used in the compositions and methods provided herein. In one embodiment, the term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al, Proc. Natl. Acad Sci. USA 81 (1984) 6851-6855; U.S. Pat. Nos. 5,202,238 and 5,204,244.

In one embodiment, a humanized antibody may be used in the compositions and methods provided herein. In some embodiments, the term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In other embodiments, the CDRs of the VH and VL are grafted into the framework region of human antibody to prepare the "humanized antibody." See e.g. Riechmann, L., et al, Nature 332 (1988) 323-327; and Neuberger, M. S., et al, Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix IP A.1P.1-A.1P.37 and are accessible via IMGT, the international ImMunoGeneTics information System® (http://imgt.cines.fr) or via http://vbase.mrc-cpe.cam.ac.uk. Optionally the framework region can be modified by further mutations. Particularly preferred CDRs correspond to those representing sequences recognizing the antigens noted above for chimeric antibodies. The term "humanized antibody" as used herein also comprises such antibodies which are modified in the constant region to generate the properties according to the invention, especially in regard to complement component 1q (C1q) binding and/or Fc Receptor (FcR) binding, e.g. by "class switching" i.e. change or mutation of Fc parts (e.g. from IgG1 to IgG4 and/or IgG1/IgG4 mutation). The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al, Proc. Natl. Acad. Sci. USA 90 (1993) 2551-2555; Jakobovits, A., et al, Nature 362 (1993) 255-258; Brueggemann, M. D., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al, J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al, J. Immunol. 147 (1991) 86-95). As already mentioned for humanized antibodies according to the invention the term "human antibody" as used herein also comprises such antibodies which are modified in the constant region to generate the properties according to the invention.

In one particular embodiment of the present invention, the mAb comprised by the recombinant fusion protein provided herein comprises at least one mutation in the Fc domain or region.

The term "recombinant human antibody", as used herein, is intended to include all human antibodies that are prepared, expressed, created or isolated by recombinant means, such as antibodies isolated from a host cell, for example a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

In some embodiments, the terms "which binds to human HER3", "which specifically binds to human HER3", or "anti-HER3 antibody" are interchangeable and refer to an antibody which specifically binds to the human HER3 antigen with a KD-value of about $4.81 \times 10^{-10}$ mol/L or lower at 25° C. The binding affinity is determined with a standard binding assay at 25° C., such as surface plasmon resonance technique (BIAcore®, GE-Healthcare Uppsala, Sweden). Thus an "antibody which binds to human HER3" as used herein refers to an antibody or portion thereof specifically which binds to the human HER3 antigen with a binding affinity within a range of KD $1.0 \times 10^{-8}$ mol/L-$1.0 \times 10^{-13}$ mol/L) at 25° C., and preferably with a KD-value of $4.81 \times 10^{-10}$ mol/L or lower at 25° C.

In another aspect, an anti-HER3 antibody comprised by the recombinant fusion protein disclosed herein comprises a variable region heavy (VH) chain and a variable region light (VL) chain. In one embodiment, the antibody comprises the VH and VL sequences in SEQ ID NO: 2 and SEQ ID NO: 3, respectively; and has one or more of the following properties: inhibition of HER3 phosphorylation in tumor cells, inhibition of AKT phosphorylation in tumor cells, inhibition of signaling through ErbB3 (HER3), and inhibition of the proliferation of tumor cells.

In one embodiment, the anti-HER3 mAb provided herein comprises a VH amino acid sequence set forth in SEQ ID NO: 2:

```
Heavy Chain:
                                            (SEQ ID NO: 2)
QVQLQQWGAG LLKPSETLSL TCAVYGGSFS GYYWSWIRQP

PGKGLEWIGE INHSGSTNYN PSLKSRVTIS VETSKNQFSL

KLSSVTAADT AVYYCARDKW TWYFDLWGRG TLVTVSSAST

KGPSVFPLAP SSKSTSGGTA ALGCLVKDYF PEPVTVSWNS

GALTSGVHTF PAVLQSSGLY SLSSVVTVPS SSLGTQTYIC

NVNHKPSNTK VDKRVEPKSC DKTHTCPPCP APEFLGGPAV

FLFPPKPKDT LMISRTPEVT CVVVDVSHED PEVKFNWYVD

GVEVHNAKTK PREEQYNSTY RVVSVLTVLH QDWLNGKEYK

CKVSNKALPA PIEKTISKAK GQPREPQVYT LPPSREEMTK

NQVSLTCLVK GFYPSDIAVE WESNGQPENN YKTTPPVLDS

DGSFFLYSKL TVDKSRWQQG NVFSCSVMHE ALHAHYTQKS

LSLSPGK.
```

In one embodiment, the anti-HER3 mAb provided herein comprises a VL amino acid sequence of SEQ ID NO: 3:

```
Light Chain:
                                            (SEQ ID NO: 3)
DIEMTQSPDS LAVSLGERAT INCRSSQSVL YSSSNRNYLA

WYQQNPGQPP KLLIYWASTR ESGVPDRFSG SGSGTDFTLT

ISSLQAEDVA VYYCQQYYST PRTFGQGTKV EIKRTVAAPS

VFIFPPSDEQ LKSGTASVVC LLNNFYPREA KVQWKVDNAL

QSGNSQESVT EQDSKDSTYS LSSTLTLSKA DYEKHKVYAC

EVTHQGLSSP VTKSFNRGEC.
```

In one embodiment, the anti-HER3 antibody of the present invention comprises at least one mutation in the Fc region. In another embodiment, the mature anti-HER3 antibody (i.e.—lacking a signal peptide) of the present invention comprises at least one mutation in amino acids 234, 239, 434, or a combination thereof, where in other embodiments, the amino acid mutations comprise at least one of the following substitution mutations: L234F, S239A, N434A or a combination thereof. In another embodiment, mutations to amino acids 234 and/or 239 knock down effector functions of the anti-HER3 antibody. In another embodiment, a mutation to amino acid 434 extends the half-life of the antibody in a subject.

In some embodiments, the one or more mutations in the Fc region reduce effector function. In some embodiments, the reduced effector function comprises a reduced affinity of the anti-HER3 antibody for one or more Fc Receptors. The FcRs can be FcγRI, FcγRIIa, FcγRIIb, FcγRIIIa (158F), FcγRIIIa (158V) and C1q. In some embodiments, the reduced affinity comprising an increase in dissociation constant of about 1 order of magnitude or greater. In some embodiments, introducing one or more Fc mutations increases the KD of the anti-HER3 antibody of fusion protein comprising same for FcγRI from $2.81 \times 10^{-9}$ M to $1.03 \times 10^{-8}$ M. In some embodiments, introducing one or more Fc mutations increases the KD of the anti-HER3 antibody of fusion protein comprising same for FcγRIIa from $3.95 \times 10^{-7}$ M to $1.35 \times 10^{-6}$ M. In some embodiments, introducing one or more Fc mutations increases the KD of the anti-HER3 antibody of fusion protein comprising same for FcγRIIb from $1.03 \times 10^{-7}$ M to $1.52 \times 10^{-6}$ M. In some embodiments, introducing one or more Fc mutations increases the KD of the anti-HER3 antibody of fusion protein comprising same for FcγRIIIa (158F) from $6.37 \times 10^{-8}$ M to $1.18 \times 10^{-7}$ M. In some embodiments, introducing one or more Fc mutations increases the KD of the anti-HER3 antibody of fusion protein comprising same for FcγRIIIa (158V) from $3.41 \times 10^{-8}$ M to $9.10 \times 10^{-8}$ M.

In some embodiments, the anti-HER3 antibody or recombinant fusion protein comprising same binds to FcγRI with an equilibrium dissociation constant (KD) higher than or equal to $1.03 \times 10^{-8}$ M. In some embodiments, the anti-HER3 antibody or recombinant fusion protein comprising same comprises one or more Fc mutations and binds to FcγRIIa with a KD higher than or equal to $1.35 \times 10^{-6}$ M. In some embodiments, the anti-HER3 antibody or recombinant fusion protein comprising same comprises one or more Fc mutations and binds to FcγRIIb with a KD higher than or equal to $1.5 \times 10^{-6}$ M. In some embodiments, the anti-HER3 antibody or recombinant fusion protein comprising same comprises one or more Fc mutations and binds to FcγRIIIa (158F) with a KD higher than or equal to $1.18 \times 10^{-7}$ M. In some embodiments, the anti-HER3 antibody or recombinant fusion protein comprising same comprises one or more Fc mutations and binds to FcγRIIIa (158V) with a KD higher than or equal to $9.10 \times 10^{-8}$ M.

The term "antibody effector function(s)" as used herein refers to a function contributed by an Fc region(s) of an Ig. Such function can be affected by, for example, binding of an Fc effector region (s) to an Fc receptor on an immune cell with phagocytic or lytic activity or by binding of an Fc effector region(s) to components of the complement system.

In one embodiment, the anti-HER3 antibody does not induce antibody-dependent cellular cytotoxicity (ADCC). The term "antibody-dependent cellular cytotoxicity (ADCC)" refers to lysis of human target cells by an antibody according to the invention in the presence of effector cells.

In one embodiment of the invention, the antibody according to the invention is glycosylated. In some embodiments, the glycosylation is N-glycosylation. In other embodiments, the glycosylation is O-glycosylation.

In the context of the recombinant fusion protein provided herein and according to the invention, the antibodies comprised by the recombinant fusion protein may be produced via recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al, Protein Expr. Purif 8 (1996) 271-282; Kaufman, R. J., Mol. Biotechnol. 16 (2000) 151-161; Werner, R. G., Drug Res. 48 (1998) 870-880. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including, column chromatography and others well known in the art (see Ausubel, F., et al, ed. Current Protocols in Molecular Biology, Greene Publishing and Wiley Interscience, New York (1987)). Expression in NS0 cells is described by, e.g., Barnes, L. M., et al, Cytotechnology 32 (2000) 109-123; Barnes, L. M., et al, Biotech. Bioeng. 73 (2001) 261-270. Transient expression is described by, e.g., Durocher, Y., et al, Nucl. Acids. Res. 30 (2002) E9. Cloning of variable domains is described by Orlandi, R., et al, Proc. Natl. Acad. Sci. USA 86 (1989) 3833-3837; Carter, P., et al, Proc. Natl. Acad. Sci. USA 89 (1992) 4285-4289; Norderhaug, L., et al, J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

It is self-evident that the antibodies are administered to the subject in therapeutically effective amount which is the amount of the subject compound or combination that will elicit the biological or medical response of a tissue, system, animal or human that is being sought by the researcher, veterinarian, medical doctor or other clinician.

Recombinant Fusion Protein—Neuregulin

In one embodiment, the recombinant fusion protein provided herein comprises a fragment of an NRG-1 protein. NRG proteins can bind to the ErbB4 receptor on the surface of myocardial cells, continuously activate the PI3K/AKT signal pathway in the cell, and change the structure of the myocardial cells, thereby improving the function of myocardial cells.

As used herein, "neuregulin" or "NRG" refers to proteins or peptides that can bind and activate ErbB3, ErbB4 or heterodimers or homodimers thereof, including neuregulin isoforms, neuregulin EGF-like domain, polypeptides comprising neuregulin EGF-like domain, neuregulin mutants or derivatives, and any kind of neuregulin-like gene products that can activate the above receptors Neuregulin also includes NRG-1, NRG-2, NRG-3 and NRG-4 proteins, peptides, fragments and compounds that have the functions of neuregulin. In preferred embodiments, neuregulin is a protein or peptide that can bind to and activate ErbB2/ErbB4 or ErbB2/ErbB3 heterodimers, for example, but not for the purpose of restriction, peptides of the present invention includes a fragment of the NRG-1β2 isoform, i.e., the 177-237 amino acid fragment, which contains the EGF-like domain having the following amino acid sequence: SHLVK-CAEKEKTFCVNGGECFMVKDLSNPSRYLCKCP-NEFTGDRCQNYVMASFYK AEELYQ (SEQ ID NO: 4). The NRG proteins of the present invention can activate the receptors above and regulate their biological functions, for example, stimulate the synthesis of acetylcholine receptors in skeletal muscle cells, promote the differentiation and survival of cardiomyocytes and DNA synthesis. It is well known to those of skill in this art that a mutation of a single amino acid in a non-critical region generally would not alter the biological activity of the resulting protein or polypeptide (see, e.g., Watson et al., Molecular Biology of the Gene, 4th Edition, 1987, The Bejacmin/Cummings Pub. co., p. 224). The NRG proteins of the invention can be isolated from natural sources, may be modified through recombination technology, artificial synthesis or other means.

As used herein, "epidermal growth factor-like domain" or "EGF-like domain" refers to a polypeptide fragment encoded by the neuregulin gene that binds to and activates ErbB3, ErbB4, or heterodimers or homodimers thereof and including heterodimers with ErbB2, and structurally similar to the EGF receptor binding region as described in WO 00/64400, Holmes et al., Science, 256:1205-1210 (1992); U.S. Pat. Nos. 5,530,109 and 5,716,930; Hijazi et al., Int. J. Oncol., 13:1061-1067 (1998); Chang et al., Nature, 387:

509-512 (1997); Carraway et al., Nature, 387:512-516 (1997); Higashiyama et al., J. Biochem., 122:675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain refers to amino acid residues 177-226, 177-237, or 177-240 of NRG-1. In certain embodiments, EGF-like domain comprises the amino acid sequence of the receptor binding domain of neuregulin-2 (NRG-2, also known in the art as DON1, HRG2 and NTAK). In certain embodiments, an EGF-like domain of NRG-2 comprises a sequence of HARKCNETAKSYCVNGGVCYYIEGINQLSCKCPNGFFGQRCL (SEQ ID NO: 15). In certain embodiments, EGF-like domain comprises the amino acid sequence of the receptor binding domain of neuregulin 3 (NRG-3, also known in the art as HRG3 and pro-NRG3). In certain embodiments, the EGF-like domain of NRG-3 comprises a sequence of HFKPCRDKDLAYCLNDGECFVIETLTGSHKHCRCKEGYQGVRCD (SEQ ID NO: 16). In certain embodiments, EGF-like domain comprises the amino acid sequence of the receptor binding domain of neuregulin 4 (NRG-4, also known in the art as HER4). In certain embodiments, an EGF-like domain of NRG-4 comprises a sequence of HEEPCGPSHKSFCLNGGLCYVIPTIPSPFCRCVENYTGARCE (SEQ ID NO: 17). In certain embodiments, EGF-like domain comprises the amino acid sequence of Ala Glu Lys Glu Lys Thr Phe Cys Val Asn Gly Glu Cys Phe Met Val Lys Asp Leu Ser Asn Pro (SEQ ID NO: 18), as described in U.S. Pat. No. 5,834,229.

In one embodiment, the NRG-1 protein provided in the recombinant fusion protein disclosed herein is the NRG-1 β2a isoform.

In some embodiments, the active NRG-1 fragment comprises the ERBB3/4 binding domain. In another related embodiment, the NRG-1 binds to and induces signaling through ErbB4 (HER4). In other embodiments, the mAb inhibits NRG-1 signaling through ErbB3 (HER3). In some embodiments, the active protein fragment of NRG-1 comprises the active domain of NRG-1.

Recombinant Fusion Protein—Compositions

In one embodiment, in the recombinant fusion protein disclosed herein the NRG-1 is fused to the C-terminus of the anti-HER3 antibody heavy chain using a linker. In another related aspect, NRG-1 is attached to the linker via the first (1$^{st}$) amino acid on the N-terminus of NRG-1, which in one embodiment is a Serine (S or Ser) amino acid. The specific recombinant fusion protein utilized in the current invention may be optionally obtained or created by any method known in the art (including purchase from commercial sources). For example, nucleic acid sequences encoding the appropriate antibody framework are optionally cloned and ligated into appropriate vectors (e.g., expression vectors for, e.g., prokaryotic or eukaryotic organisms). Additionally, nucleic acid sequences encoding the NRG-1 β2a isoform molecule are optionally cloned into the same vector in the appropriate orientation and location so that expression from the vector produces an antibody-NRG-1 β2a isoform fusion protein. Some optional embodiments also require post-expression modification, e.g., assembly of antibody subunits, etc. The techniques and art for the above (and similar) manipulations are well known to those skilled in the art. Pertinent instructions are found in, e.g., Sambrook et al., Molecular Cloning—A Laboratory Manual (2nd Ed.), Vols. 1-3, Cold Spring Harbor Laboratory, Cold Spring Harbor, N.Y., 1989 and Current Protocols in Molecular Biology, F. M. Ausubel et al., eds., Current Protocols, a joint venture between Greene Publishing Associates, Inc. and John Wiley & Sons, Inc. (supplemented through 1999). In some alternate embodiments, the antibody domain and NRG-1 β2a isoform are assembled post-expression through, e.g., chemical means. In one embodiment, the present invention provides a composition, e.g. a pharmaceutical composition comprising the recombinant fusion protein of the present invention.

In one embodiment, the recombinant fusion protein promotes cardiomyocyte proliferation, differentiation, and survival. In another embodiment, the recombinant fusion protein promotes proliferation, differentiation and survival of cardiac tissue. In one embodiment, the recombinant fusion protein promotes cardiomyocyte proliferation, differentiation, and survival without promoting cancer and/or tumor growth. In another embodiment, the recombinant fusion protein promotes proliferation, differentiation and survival of cardiac tissue without promoting cancer or tumor growth.

In one embodiment, the cancer is adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstroem macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, soft tissue sarcoma, epithelioid sarcoma, synovial sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, or Wilm's Tumor.

In another embodiment, the recombinant fusion protein promotes proliferation, differentiation and survival of central nervous system (CNS) cells. In another embodiment, the recombinant fusion protein promotes proliferation, differentiation and survival of central nervous system (CNS) cells without promoting cancer and/or tumor growth. In another embodiment, the recombinant fusion protein has a reduced capacity to induce antibody-dependent cell cytotoxicity (ADCC).

In some embodiments, the recombinant fusion protein promotes HER2/4 signaling over HER2/3 signaling relative to the signal induction potential of recombinant NRG-1.

In a particular embodiment of the invention, the recombinant fusion protein comprises an anti-HER3mAb fused to or operably linked to the C-terminus of the antibody heavy chain via a GGGGSGGGGS (G45) linker (SEQ ID NO: 5) to the NRG-1 β2a isoform of SEQ ID NO: 4. In some embodiments, one or more copies of the linker may be used. In other embodiments, 2, 3, 4, or 5 copies of the G45 linker or any other linker known in the art as being suitable for the composition disclosed herein may be used herein.

The term "linker" is art-recognized and refers to a molecule (including but not limited to unmodified or modified nucleic acids or amino acids) or group of molecules (for example, 2 or more, e.g., 2, 3, 4, 5, 6, 7, 8, 9, 10, 15, 20, 25, 30, 35, 40, 45, 50, 55, 60, 65, 70, 75, 80, 85, 90, 95, 100 or more) connecting two compounds, such as two polypeptides. The linker may be comprised of a single linking molecule or may comprise a linking molecule and at least one spacer molecule, intended to separate the linking molecule and a compound by a specific distance.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader contiguous and in reading frame. However, enhancers are optionally contiguous. Linking can be accomplished, for example, by ligation at convenient restriction sites. If such sites do not exist, synthetic oligonucleotide adaptors, linkers or other methods known in the art can be used. In another embodiment, the "operably linked" also refers to the functional pairing of distinct amino acid sequences, peptides or proteins, as in the pairing of the antibody and NRG-1 fragment described herein via a linker sequence also described herein.

In another embodiment, the anti-HER3 mAb heavy chain comprised by the recombinant fusion protein provided herein is encoded by SEQ ID NO: 6:
ATGGAGTTTGGGCTGAGCTGGGTTTTCCTTGTTGC-TATAATAAAAGGTGTCCAGT
GTCAGGTGCAGCTGCAGCAGTGGG-GAGCTGGACTGCTGAAGCCAAGCGAGACCC
TGTCTCTGACATGCGCCGTGTACGGAG-GATCCTTCAGCGGATACTATTGGTCTTG
GATCAGGCAGCCACCTGGCAAGGGACTGGAGTG-GATCGGCGAGATCAACCACTC TGGCTCCACCAAC-TACAATCCCTCTCTGAAGTCCCGGGTGAC-CATCTCCGTGGAG
ACAAGCAAGAATCAGTTTTCCCT-GAAGCTGTCCAGCGTGACCGCCGCTGACACA
GCCGTGTACTAT-TGCGCTAGGGACAAGTGGACCTGGTATTTC-GATCTGTGGGGAA
GGGGCACCCTGGTGACAGTGTCTTCCGCCTCTA-CAAAGGGCCCCTCCGTGTTTCC TCTGGCTC-CAAGCTCTAAGAGCACCTCTGGAG-GAACAGCCGCTCTGGGATGTCTG
GTGAAGGATTACTTCCCTGAGCCAGTGACCGT-GAGCTGGAACTCTGGCGCCCTGA CCTCCGGAGTG-CATACATTTCCCGCTGTGCTGCAGTCCA
GCGGCCTGTATAGCCT
GTCTTCCGTGGTGACCGTGCCTAGCTCTTCCCTGG-GCACCCAGACATACATCTGC AACGTGAAT-CACAAGCCCTCCAATA-CAAAGGTGGACAAGAGAGTGGAGCCTAAG
AGCTGTGATAAGACCCATACATGCCCAC-CATGTCCAGCTCCTGAGCTGCTGGGAG
GACCTTCCGTGTTCCTGTTTCCTCCAAAGC-CAAAGGACACCCTGATGATCTCTCG CACCCCT-GAGGTGACATGCGTGGTGGTGGACGTGTCC-CACGAGGATCCAGAGGT
GAAGTTCAACTGGTACGTGGATGGCGTGGAGGTG-CATAATGCTAAGACCAAGCC TAGGGAG-GAGCAGTACAACAGCACC-TATCGGGTGGTGTCTGTGCTGACAGTGCT
GCACCAGGACTGGCTGAACGGCAAGGAGTA-CAAGTGCAAGGTGAGCAATAAGG
CCCTGCCAGCTCCCATCGAGAAGAC-CATCTCTAAGGCCAAGGGCCAGCCCAGAG
AGCCTCAGGTGTATACACTGCCCCCTAGCCGCGAG-GAGATGACCAAGAACCAGG TGTCTCTGA-CATGTCTGGTGAAGGGCTTCTACCCATCTGA-CATCGCTGTGGAGTG
GGAGTCCAATGGCCAGCCCGAGAACAATTATAA-GACCACACCACCCGTGCTGGA CTCC-GATGGCAGCTTCTTTCTGTACTC-CAAGCTGACCGTGGATAAGAGCAGGTGG
CAGCAGGGCAACGTGTTTTCCTGCAGCGT-GATGCACGAGGCCCTGCACAATCATT ATA-CACAGAAATCTCTGTCCCTGAGCCCAGGCAAGG-GAGGAGGAGGAAGCGGA
GGAGGAGGCAGCTCTCATCTGGTGAAGTGTGCT-GAGAAGGAGAAGACCTTCTGC
GTGAACGGCGGCGAGTGTTTTATGGT-GAAGGACCTGTCTAATCCATCCAGATACC TGTGCAAGTGTCCCAACGAGTTCACAGGC-GATCGCTGCCAGAATTACGTGATGGC CTCTTTT-TATAAGGCTGAGGAGCTGTACCAGTAA (SEQ ID NO: 6). In one embodiment, the sequence set forth in SEQ ID NO: 6 comprises no Fc mutations. In one embodiment, SEQ ID NO: 6 is also referred to as "NPCF".

In one embodiment, the recombinant fusion protein provided herein comprises a heavy chain of an anti-HER3 mAb. In another embodiment, the anti-HER3 mAb heavy chain is encoded by SEQ ID NO: 7:
ATGGAGTTTGGGCTGAGCTGGGTTTTCCTTGTTGC-TATAATAAAAGGTGTCCAGT
GTCAGGTGCAGCTGCAGCAGTGGG-GAGCTGGACTGCTGAAGCCAAGCGAGACCC
TGTCTCTGACATGCGCCGTGTACGGAG-GATCCTTCAGCGGATACTATTGGTCTTG
GATCAGGCAGCCACCTGGCAAGGGACTGGAGTG-GATCGGCGAGATCAACCACTC TGGCTCCACCAAC-TACAATCCCTCTCTGAAGTCCCGGGTGAC-CATCTCCGTGGAG
ACAAGCAAGAATCAGTTTTCCCT-GAAGCTGTCCAGCGTGACCGCCGCTGACACA
GCCGTGTACTAT-TGCGCTAGGGACAAGTGGACCTGGTATTTC-GATCTGTGGGGAA
GGGGCACCCTGGTGACAGTGTCTTCCGCCTCTA-CAAAGGGCCCCTCCGTGTTTCC TCTGGCTC-CAAGCTCTAAGAGCACCTCTGGAG-GAACAGCCGCTCTGGGATGTCTG
GTGAAGGATTACTTCCCTGAGCCAGTGACCGT-GAGCTGGAACTCTGGCGCCCTGA CCTCTGGAGTG-CATACATTTCCCGCTGTGCTGCAGT
CCAGCGGCCTGTATAGCCT
GTCTTCCGTGGTGACCGTGCCTAGCTCTTCCCTGG-GCACCCAGACATACATCTGC AACGTGAAT-CACAAGCCCTCCAATA-CAAAGGTGGACAAGAGAGTGGAGCCTAAG
AGCTGTGATAAGACCCATACATGCCCAC-CATGTCCAGCTCCTGAGTTCCTGGGAG
GACCTGCCGTGTTCCTGTTTCCTCCAAAGC-CAAAGGACACCCTGATGATCTCTCG CACCCCT-GAGGTGACATGCGTGGTGGTGGACGTGTCC-CACGAGGATCCAGAGGT
GAAGTTCAACTGGTACGTGGATGGCGTGGAGGTG-CATAATGCTAAGACCAAGCC TAGGGAG-GAGCAGTACAACAGCACC-TATCGGGTGGTGTCTGTGCTGACAGTGCT
GCACCAGGACTGGCTGAACGGCAAGGAGTA-CAAGTGCAAGGTGAGCAATAAGG
CCCTGCCAGCTCCCATCGAGAAGAC-CATCTCTAAGGCCAAGGGCCAGCCCAGAG
AGCCTCAGGTGTATACACTGCCCCCTAGCCGCGAG-GAGATGACCAAGAACCAGG
TGTCTCTGACCTGTCTGGTGAAGGGCTTCTACC-CATCTGACATCGCTGTGGAGTG GGAGTC-CAATGGCCAGCCCGAGAACAATTATAAGAC-CACACCACCCGTGCTGGA
CTCCGATGGCAGCTTCTTTCTGTACTC-CAAGCTGACCGTGGATAAGAGCAGGTGG
CAGCAGGGCAACGTGTTTTCCTGCAGCGT-GATGCACGAGGCCCTGCACGCTCATT ATA-CACAGAAATCTCTGTCCCTGAGCCCAGGCAAGG-GAGGAGGAGGAAGCGGA
GGAGGAGGCAGCTCTCATCGGTGAAGTGTGCT-GAGAAGGAGAAGACCTTCTGC
GTGAACGGCGGCGAGTGTTTTATGGT-GAAGGACCTGTCTAATCCATCCAGATACC TGTGCAAGTGTCCCAACGAGTTCACAGGC-GATCGCTGCCAGAATTACGTGATGGC CTCTTTT-TATAAGGCTGAGGAGCTGTACCAGTAA (SEQ ID NO: 7). In one embodiment, SEQ ID NO: 7 is also referred to as "NPCFA". In one embodiment, SEQ ID NO: 7 comprises one or more mutations that encode for one or more mutations in the constant (Fc) region of the anti-HER3 mAb provided herein. In one embodiment, the mature anti-HER3 antibody of the present invention comprises at least one mutation in amino acids 234, 239, 434, or a combination thereof. In another embodiment, the amino acid mutations comprise at least one of the following substitution mutations: L234F, S239A, N434A or a combination thereof.

In one embodiment, the recombinant fusion protein provided herein comprises a light chain sequence of an anti-HER3 mAb. In another embodiment, the light chain sequence is encoded by (SEQ ID NO: 8):
ATGGTGTTGCAGACCCAGGTCTTCAT-TTCTCTGTTGCTCTGGATCTCTGGTGCCTA
CGGGGACATCGAGATGACCCAGTCTCCAGAT-TCCCTGGCCGTGAGCCTGGGAGA GAGGGCTA-CAATCAACTGCCGGTCCAGCCAGTCTGTGCTGT
ACTCTTCCAGCAAC AGGAAT-TACCTGGCCTGGTATCAGCAGAATCCCGGCCAGCC-CCCTAAGCTGCTGA TCTAT-TGGGCTAGCACCAGAGAGTCTG-GAGTGCCTGACCGCTTCTCTGGATCCGG
AAGCGGCACAGACTT-CACCCTGACAATCTCTTCCCTGCAGGCCGAGGACG
TGGCC GTGTACTATTGCCAGCAGTATTACTC-TACCCCTAGGACATTCGGCCAGGGCACCA AGGTG-GAGATCAAGCGGACAGTGGCCGCTCCATCCGTGTT-CATCTTTCCACCCTC
CGACGAGCAGCTGAAGTCCG-GAACCGCTAGCGTGGTGTGCCTGCTGAACAACTT
CTACCCAAGAGAGGCCAAGGTGCAGTGGAAGGTG-GATAACGCTCTGCAGAGCGG CAATTCTCAG-GAGTCCGTGACCGAGCAGGACAGCAAGGATTCTA-CATATTCCCTG
AGCTCTACCCTGACACTGTCCAAGGCCGAT-TACGAGAAGCACAAGGTGTATGCTT
GCGAGGTGACC-CATCAGGGCCTGTCCAGCCCCGTGACAAAGAGCTT-CAACCGCG GCGAGTGTTAA (SEQ ID NO: 8). In one embodiment, SEQ ID NO: 8 is also referred to as "PAL".

In one embodiment, the heavy chain of the anti-HER3 antibody comprised by the recombinant fusion protein provided herein comprises the following amino acid sequence:

(SEQ ID NO: 9)
MEFGLSWVFLVAIIKGVQCQVQLQQWGAGLLKPSETLSLTCAVYGGS

FSGYYWSWIRQPPGKGLEWIGEINHSGSTNYNPSLKSRVTISVETSKNQF

SLKLSSVTAADTAVYYCARDKWTWYFDLWGRGTLVTVSSASTKGPSVFPL

APSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

-continued

HEALHNHYTQKSLSLSPGKGGGGSGGGGSSHLVKCAEKEKTFCVNGGECF

MVKDLSNPSRYLCKCPNEFTGDRCQNYVMASFYKAEELYQ.

In one embodiment, the heavy chain of the anti-HER3 antibody comprised by the recombinant fusion protein provided herein comprises the following amino acid sequence:

(SEQ ID NO: 10)
MEFGLSWVFLVAIIKGVQCQVQLQQWGAGLLKPSETLSLTCAVYGGSFSG

YYWSWIRQPPGKGLEWIGEINHSGSTNYNPSLKSRVTISVETSKNQFSLK

LSSVTAADTAVYYCARDKWTWYFDLWGRGTLVTVSSASTKGPSVFPLAPS

SKSTSGGTAALGCLVKDYFPEPVTVSWNSGALTSGVHTFPAVLQSSGLYS

LSSVVTVPSSSLGTQTYICNVNHKPSNTKVDKRVEPKSCDKTHTCPPCPA

PEFLGGPAVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMHEA

LHAHYTQKSLSLSPGKGGGGSGGGGSSHLVKCAEKEKTFCVNGGECFMVK

DLSNPSRYLCKCPNEFTGDRCQNYVMASFYKAEELYQ.

In one embodiment, the anti-HER3 mAb heavy chain sequence comprises a signal peptide sequence. In another embodiment, the anti-HER3 mAb heavy chain signal peptide sequence comprises the amino acid sequence of MEFGLSWVFLVAIIKGVQC (SEQ ID NO: 11).

In one embodiment, light chain of the anti-HER3 antibody comprised by the recombinant fusion protein comprises the following amino acid sequence:

(SEQ ID NO: 12)
MVLQTQVFISLLLWISGAYGDIEMTQSPDSLAVSLGERATINCRSSQSV

LYSSSNRNYLAWYQQNPGQPPKLLIYWASTRESGVPDRFSGSGSGTDFTL

TISSLQAEDVAVYYCQQYYSTPRTFGQGTKVEIKRTVAAPSVFIFPPSDE

QLKSGTASVVCLLNNFYPREAKVQWKVDNALQSGNSQESVTEQDSKDSTY

SLSSTLTLSKADYEKHKVYACEVTHQGLSSPVTKSFNRGEC.

In one embodiment, the anti-HER3 mAb light chain sequence comprises a signal peptide sequence. In another embodiment, the anti-HER3 mAb light chain signal peptide sequence comprises the amino acid sequence of MVLQTQVFISLLLWISGAYG (SEQ ID NO: 13). In one embodiment, a mature polypeptide such as an antibody heavy chain or light chain amino acid sequence disclosed herein lacks a signal peptide.

In one embodiment, the recombinant fusion protein comprises the following amino acid sequences:

Heavy chain
QVQLQQWGAGLLKPSETLSLTCAVYGGSFSGYYWSWIRQPPGKGLE

WIGEINHSGSTNYNPSLKSRVTISVETSKNQFSLKLSSVTAADTAVYYCA

RDKWTWYFDLWGRGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPEFLGGPAVFLFPPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHAHYTQKSLSLSPG

K*GGGGSGGGGS*SHLVKCAEKEKTFCVNGGECFMVKDLSNPSRYLCKCPN

EFTGDRCQNYVMASFYKAEELYQ (SEQ ID NO: 14, wherein bold italics indicate the linker, and bold indicates the NRG-1 fragment);
and Light chain
(SEQ ID NO: 3)
DIEMTQSPDSLAVSLGERATINCRSSQSVLYSSSNRNYLAWYQQNPGQPP

KLLIYWASTRESGVPDRFSGSGSGTDFTLTISSLQAEDVAVYYCQQYYST

PRTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC.

In one embodiment, each of the heavy chain sequence and light chain sequence in the mature recombinant fusion protein lack a signal peptide amino acid sequence.

In a particular embodiment of the invention, the heavy chain of the anti-HER3 antibody provided herein is fused via the C-terminus linker sequence to the NRG-1 β2a isoform provided herein. In another embodiment, the C-terminus of the antibody heavy chain comprises the Fc domain of the antibody.

In some embodiments, provided are pharmaceutical compositions comprising the recombinant fusion protein disclosed herein formulated together with a pharmaceutical carrier.

In some embodiments, the anti-HER3 antibody and the NRG-1 fragment described herein are recombinantly or chemically fused/operably linked via a linker to form a fusion protein. A "fusion protein," "fusion polypeptide," "recombinant fusion protein," or "recombinant polypeptide" refers to a hybrid polypeptide which comprises polypeptide portions from at least two different polypeptides. A "fusion protein" as defined herein, is a fusion of a first amino acid sequence (protein) comprising, for example an NRG-1 β2a isoform of the invention, joined via a linker to the C-terminus of a second amino acid sequence comprising an heavy chain of an antibody that binds specifically to ERBB3 (HER3).

In one embodiment, the fusion protein is recombinantly encoded and produced. In some embodiments, the recombinant fusion protein is encoded by a nucleic acid sequence encoding the antibody of the invention that is operably linked via a nucleic acid sequence encoding a linker, to a nucleic acid sequence encoding an NRG-1 β2a isoform of the invention.

In one embodiment, the recombinant fusion protein amino acid sequence is homologous to SEQ ID NO: 14 fused to SEQ ID NO: 3. The term "homology" may refer to identity to recombinant fusion protein sequence (e.g. to any of SEQ ID NO: 1-18) of greater than 70%. In another embodiment, "homology" refers to identity to any of SEQ ID NO: 1-18 of greater than 72%. In another embodiment, "homology" refers to identity to any of SEQ ID NO: 1-18 of greater than 75%. In another embodiment, "homology" refers to identity to any of SEQ ID NO: 1-18 of greater than 78%. In another embodiment, "homology" refers to identity to any of SEQ ID NO: 1-18 of greater than 80%. In another embodiment, "homology" refers to identity to any of SEQ ID NO: 1-18 of greater than 82%. In another embodiment, "homology" refers to identity to any of SEQ ID NO: 1-18 of greater than 83%. In another embodiment, "homology" refers to identity to any of SEQ ID NO: 1-18 of greater than 85%. In another embodiment, "homology" refers to identity to any of SEQ ID NO: 1-18 of greater than 87%. In another embodiment, "homology" refers to identity to any of SEQ ID NO: 1-18 of greater than 88%. In another embodiment, "homology" refers to identity to any of SEQ ID NO: 1-18 of greater than 90%. In another embodiment, "homology" refers to identity to any of SEQ ID NO: 1-18 of greater than 92%. In another embodiment, "homology" refers to identity to any of SEQ ID NO: 1-18 of greater than 93%. In another embodiment, "homology" refers to identity to any of SEQ ID NO: 1-18 of greater than 95%. In another embodiment, "homology" refers to identity to any of SEQ ID NO: 1-18 of greater than 96%. In another embodiment, "homology" refers to identity to any of SEQ ID NO: 1-18 of greater than 97%. In another embodiment, "homology" refers to identity to any of SEQ ID NO: 1-18 of greater than 98%. In another embodiment, "homology" refers to identity to any of SEQ ID NO: 1-18 of greater than 99%. In another embodiment, "homology" refers to identity to any of SEQ ID NO: 1-18 of 100%.

The determination of percent identity between two sequences can be accomplished using a mathematical algorithm. A non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to a protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (id.). When utilizing BLAST, Gapped BLAST, and PSI-BLAST programs, the default parameters of the respective programs (e.g., XBLAST and NBLAST) can be used. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

In some embodiments, polynucleotides of the present invention are prepared using PCR techniques using procedures and methods known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancer) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence.

In some embodiments, non-bacterial expression systems are used (e.g., mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vectors of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, the expression vectors of the present invention include elements that increase the expression of the recombinant fusion proteins of the invention. Such features include, but are not limited to, choice of promoter and polyadenylation. In some embodiments, the polyadenylation sequence is a bovine growth hormone (BGH) polyadenylation sequence. In some embodiments, the promoter comprises a constitutively active promoter. In some embodiments, the promoter comprises a cytomegalovirus promoter (pCMV).

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Barr virus include pHEBO, and p205. Other exemplary vectors include pMSG, pAV009/A⁺, pMTO10/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector encoding the recombinant fusion protein of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, transformed cells are cultured under effective conditions, which allow for the expression of high amounts of recombinant fusion protein or polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in E. coli; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In some embodiments, the recombinant polypeptides are synthesized and purified; their therapeutic efficacy can be assayed in vivo or in vitro.

In one embodiment, the pharmaceutical composition provided herein comprising the recombinant fusion protein of the invention is further formulated with a pharmaceutical carrier. As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

Therapeutic Methods

In one embodiment, the present invention provides a method of treating a disease or condition in a subject in need thereof, the method comprising administering a therapeutically effective amount of the recombinant fusion protein or the pharmaceutical composition comprising the recombinant fusion protein disclosed herein.

In one embodiment, the present invention provides a method of treating a cardiovascular disease or condition in a subject in need thereof, the method comprising administering a therapeutically effective amount of the recombinant fusion protein or a pharmaceutical composition comprising the same.

In one embodiment, the present invention provides a method of preventing, inhibiting, suppressing or delaying the onset of a cardiovascular disease or condition in a subject, the method comprising administering an effective amount of the recombinant fusion protein or the pharmaceutical composition described herein.

In some embodiments, the cardiovascular disease comprises a chronic heart failure/Congestive heart failure (CHF), acute heart failure/myocardial infarction (MI), left ventricular systolic dysfunction, reperfusion injury associated with MI, chemotherapy-induced cardiotoxicity (adult or pediatric), radiation-induced cardiotoxicity, adjunct to surgical intervention in pediatric congenital heart disease.

In some embodiments, the wherein the chemotherapy-induced cardiotoxicity results from a subject receiving anthracyclines, alkylating agents, antimicrotubule agents, and antimetabolites agents used as chemotherapy.

In some embodiments, the cardiovascular condition is cardiotoxicity as a result of a subject receiving a cancer therapy. In other embodiments, the cancer therapy is a HER-2 targeted therapy. In other embodiments, the HER-2 targeted therapy comprises use of trastuzumab, ado-trastuzumab, emtansine, lapatinib, neratinib, and pertuzumab, any anti-HER2 antibody, any anti-HER2 agent or a combination thereof.

In another aspect, the invention relates to a method of inducing remodeling of muscle cell sarcomeric and cytoskeleton structures, or cell-cell adhesions, the method comprising treating the cells with the recombinant fusion protein disclosed herein.

In one embodiment, the therapeutic method is directed to treating heart failure resulting from disassociation of cardiac muscle cell-cell adhesion and/or the disarray of sarcomeric structures in the mammal.

In another aspect, the present invention provides a method for preventing, treating or delaying heart failure with preserved ejection fraction in a human, the method comprising administering a pharmaceutical composition comprising a recombinant fusion protein disclosed herein.

As used herein, the term "ejection fraction" refers to Ejection fraction (EF), a measurement, typically expressed as a percentage, of how much blood the left ventricle pumps out with each contraction. For example, an ejection fraction of 50 percent means that 50 percent of the total amount of blood in the left ventricle is pushed out with each heartbeat.

The invention is directed to treating subjects with or at risk for development of heart disease and related conditions, e.g., heart failure.

By the term "heart failure" is meant an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischaemic heart disease, idiopathic dilated cardiomyopathy, and myocarditis. The heart failure can be caused by any number of factors, including ischaemic, congenital, rheumatic, or idiopathic forms. Chronic cardiac hypertrophy is a significantly diseased state which is a precursor to congestive heart failure and cardiac arrest.

In one embodiment, "treatment" refers to both therapeutic treatment and prophylactic or preventative measures, wherein the object is to prevent or slow down (lessen) heart hypertrophy. Those in need of treatment include those already with the disorder as well as those prone to have the disorder or those in which the disorder is to be prevented. The heart hypertrophy may be from any cause which is responsive to retinoic acid, including congenital, viral, idiopathic, cardiotrophic, or myotrophic causes, or as a result of ischaemia or ischaemic insults such as myocardial infarction. Typically, the treatment is performed to stop or slow the progression of hypertrophy, especially after heart damage, such as from ischaemia, has occurred. Preferably, for treatment of myocardial infarctions, the pharmaceutical composition provided herein is given immediately after the myocardial infarction, to prevent or lessen hypertrophy.

In some embodiments, treating a subject with a pharmaceutical composition comprising the recombinant fusion protein provided herein can result in increase in average survival time of a population of treated subjects in comparison to a population receiving monotherapy with a drug that is not a compound of the disclosure, or a pharmaceutically acceptable salt, solvate, analog or derivative thereof. Preferably, after treatment with the strategies, treatment modalities, methods, combinations, and compositions provided herein, the average survival time is increased by more than 30 days; more preferably, by more than 60 days; more preferably, by more than 90, 120, or 365 days; more preferably, by more than 365 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with the pharmaceutical composition disclosed herein.

In some embodiments, treating a subject with a pharmaceutical composition comprising the recombinant fusion protein provided herein can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the disclosure, or a pharmaceutically acceptable salt, solvate, analog or derivative thereof. Preferably, after treatment with the strategies, treatment modalities, methods, combinations, and compositions provided herein, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with the pharmaceutical composition disclosed herein.

In one embodiment, the present invention provides a method of treating a central nervous system (CNS)-related disease or condition in a subject in need thereof, the method comprising administering a therapeutically effective amount of the recombinant fusion protein or the pharmaceutical composition described herein.

In one embodiment, the present invention provides a method of preventing, inhibiting, suppressing or delaying the onset of a CNS-related disease or condition in a subject, the method comprising administering an effective amount of the recombinant fusion protein or the pharmaceutical composition described herein.

In some embodiments, the CNS-related disease or condition is amyotrophic lateral sclerosis (ALS), Parkinson's disease, Alzheimer's Disease, Bell's Palsy, epilepsy and seizures, Guillain-Barre Syndrome, stroke, traumatic brain injury, multiple sclerosis or a combination.

Administration, Dosing

A composition of the present invention can be parenterally administered to a subject in need thereof, or can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

In typical embodiments, preparations for administration to subjects include sterile aqueous or non-aqueous solutions, suspensions, and emulsions. Some embodiments include non-aqueous solvents such as propylene glycol, polyethylene glycol, vegetable oils (e.g., olive oils), organic esters (e.g., ethyl oleate) and other solvents known to those of skill in the art. Physiologically acceptable carriers (or excipients) are optionally used in certain embodiments of the invention. Examples of such include, e.g., saline, PBS, Ringer's solution, lactated Ringer's solution, etc. Additionally, preservatives and additives are optionally added to the compositions to help ensure stability and sterility. For example, antibiotics and other bacteriocides, antioxidants, chelating agents, and the like are all optionally present in various embodiments of the compositions herein.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

The recombinant fusion protein, or pharmaceutical composition comprising the same are optionally administered to subjects in need of treatment (either therapeutically or prophylactically) in any appropriate sterile pharmaceutical carrier. Such pharmaceutical carrier acts to maintain the solubility and action of the fusion protein. In some embodiments, it may be desired to administer additional components in conjunction with the fusion protein. For example, in some treatment regimes, chemotherapeutic agents, antibiotics, additional formulations comprising the recombinant fusion protein of the invention and one or more standard of care agents, etc. are all optionally included with the compositions of the invention.

As used herein, the terms "combination treatment," "combination therapy," and "co-therapy" are used interchangeably and generally refer to treatment modalities featuring an recombinant fusion protein or pharmaceutical composition comprising the same as provided herein and an additional therapeutic agent. Typically, combination treatment modalities are part of a specific treatment regimen intended to provide a beneficial effect from the concurrent action of the therapeutic agent combination. The beneficial effect of the combination may include, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). In some embodiments, combination treatment comprises administration of two or more therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, separate dosage forms for the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. The therapeutic agents can be administered according to the same or to a different administration interval. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection.

In some embodiments, combination therapy also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In some embodiments, the additional therapeutic agent is a chemotherapeutic agent (also referred to as an anti-neoplastic agent or anti-proliferative agent), e.g., an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, an immune checkpoint inhibitor, a platinum based antineoplastic agent, a CDK inhibitor, a PARP inhibitor or any anti-neoplastic or anti-proliferative agent known to those of skill in the art.

Exemplary alkylating agents suitable for use according to the combination treatment modalities provided herein include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary suitable anthracyclines include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rittman); cetuximab (Erbitux); panitumumab (Vectibix); tositumomab/iodine-131 tositumomab (Bexxar); alemtuzumab (Campath); ibritumomab (Zevalin; In-111; Y-90 Zevalin); gemtuzumab (Mylotarg); eculizumab (Soliris) or denosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (EMD 72000) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/fasudil hydrochloride; flavopiridol; seliciclib (CYC202; Roscovitine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rittman); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin), sorafenib (Nexavar), sunitinib (Sutent), ranibizumab, pegaptanib, or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary immune checkpoint inhibitors include programmed cell death 1 (PD-1), CD274 molecule (PD-L1) and cytotoxic T-lymphocyte associated protein 4 (CTLA4) inhibitors. Exemplary PD-1 inhibitors include Pembrolizumab, Nivolumab and Cemiplimab. Exemplary PD-L1 inhibitors include Atezolizumab, Avelumab and Durvalumab. Exemplary CLTA4 inhibitors include Ipilimumab.

Exemplary platinum based antineoplastic agents include Cisplatin and Carboplatin.

Exemplary cyclin dependent kinase (CDK) inhibitors include abemaciclib, palbociclib, and ribociclib.

Exemplary poly (ADP-ribose) polymerase (PARP) inhibitors include talazoparib, olaparib, rucaparib, niraparib and veliparib.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In some embodiments, combination treatment modalities are provided in which the additional therapeutic agent is a cytokine, e.g., G-CSF (granulocyte colony stimulating factor). In another aspect, a pharmaceutical composition provided herein may be administered in combination with radiation therapy. Radiation therapy can also be administered in combination with a pharmaceutical composition provided herein and another chemotherapeutic agent described herein as part of a multi-agent therapy. In yet another aspect, a pharmaceutical composition provided herein may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In some preferred embodiments, a pharmaceutical composition provided herein may be administered with an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevec (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/1apatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-B, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

In another embodiment, the recombinant fusion protein or pharmaceutical composition comprising the same polypeptide disclosed herein is administered to a subject once a day. In some embodiments, the recombinant fusion protein or pharmaceutical composition comprising the same is administered to a subject once every two days. In another embodiment, the recombinant fusion protein or pharmaceutical composition comprising the same is administered to a subject once every three days. In another embodiment, the recombinant fusion protein or pharmaceutical composition comprising the same is administered to a subject once every four days. In another embodiment, the recombinant fusion protein or pharmaceutical composition comprising the same is administered to a subject once every five days. In another embodiment, the recombinant fusion protein or pharmaceutical composition comprising the same polypeptide is administered to a subject once every six days. In another embodiment, the recombinant fusion protein or pharmaceutical composition comprising the same is administered to a subject once every week. In another embodiment, the recombinant fusion protein or pharmaceutical composition comprising the same is administered to a subject once every 7-14 days. In another embodiment, the recombinant fusion protein or pharmaceutical composition comprising the same is administered to a subject once every 10-20 days. In another embodiment, the recombinant fusion protein or pharmaceutical composition comprising the same is administered to a subject once every 5-15 days. In another embodiment, the recombinant fusion protein or pharmaceutical composition comprising the same is administered to a subject once every 15-30 days.

In one embodiment, a dose of the recombinant fusion protein of the present invention comprises from 0.005 to 0.1 milligrams/kg in an injectable solution. In another embodiment, the dose comprises from 0.005 to 0.5 milligrams/kg of the recombinant fusion protein. In another embodiment, the dose comprises from 0.05 to 0.1 micrograms of the recombinant fusion protein. In another embodiment, the dose comprises from 0.005 to 0.1 milligrams/kg of the recombinant fusion protein in an injectable solution.

In another embodiment, the recombinant fusion protein or pharmaceutical composition comprising the same is administered to a subject in a dose ranging from 0.0001 mg to 0.6 mg. In another embodiment, the recombinant fusion protein or pharmaceutical composition comprising the same is administered to a subject in a dose ranging from 0.001 mg to 0.005 mg. In another embodiment, the recombinant fusion protein or pharmaceutical composition comprising the same is administered to a subject in a dose ranging from 0.005 mg to 0.01 mg. In another embodiment, the recombinant fusion protein or pharmaceutical composition comprising the same is administered to a subject in a dose ranging from 0.01 mg to 0.3 mg. In another embodiment, the recombinant fusion protein or pharmaceutical composition comprising the same is administered to a subject in a dose ranging from 0.2 mg to 0.6 mg.

In another embodiment, the recombinant fusion protein or pharmaceutical composition comprising the same is administered to a subject in a dose ranging from 1-100 mcg/kg. In another embodiment, the recombinant fusion protein or pharmaceutical composition comprising the same is administered to a subject in a dose ranging from 10-80 mcg/kg. In another embodiment, the recombinant fusion protein or pharmaceutical composition comprising the same is administered to a subject in a dose ranging from 20-60 mcg/kg. In another embodiment, the recombinant fusion protein or pharmaceutical composition comprising the same is administered to a subject in a dose ranging from 10-50 mcg/kg. In another embodiment, the recombinant fusion protein or pharmaceutical composition comprising the same is administered to a subject in a dose ranging from 40-80 mcg/kg. In another embodiment, the recombinant fusion protein or pharmaceutical composition comprising the same is administered to a subject in a dose ranging from 10-30 mcg/kg. In another embodiment, the recombinant fusion protein or pharmaceutical composition comprising the same is administered to a subject in a dose ranging from 30-60 mcg/kg.

In another embodiment, the recombinant fusion protein or pharmaceutical composition comprising the same is administered to a subject in a dose ranging from 0.1 mcg/kg to 100 mg/kg. In another embodiment, the recombinant fusion protein or pharmaceutical composition comprising the same is administered to a subject in a dose ranging from 0.1 mcg/kg to 50 mg/kg. In another embodiment, the recombinant fusion protein or pharmaceutical composition comprising the same is administered to a subject in a dose ranging from 0.1 mcg/kg to 25 mg/kg. In another embodiment, the recombinant fusion protein or pharmaceutical composition comprising the same is administered to a subject in a dose ranging from 0.1 mcg/kg to 10 mg/kg. In another embodiment, the recombinant fusion protein or pharmaceutical composition comprising the same is administered to a subject in a dose ranging from 0.1 mcg/kg to 5 mg/kg. In another embodiment, the recombinant fusion protein or pharmaceutical composition comprising the same is administered to a subject in a dose ranging from 0.1 mcg/kg to 1 mg/kg. In another embodiment, the recombinant fusion protein or pharmaceutical composition comprising the same is administered to a subject in a dose ranging from 0.1 mcg/kg to 0.1 mg/kg. In another embodiment, the recombinant fusion protein or pharmaceutical composition comprising the same is administered to a subject in a dose ranging from 10 mg/kg to 60 mg/kg.

In another embodiment, the recombinant fusion protein or pharmaceutical composition comprising the same is administered to a subject in a dose of about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg or about 70 mg/kg.

In another embodiment, the recombinant fusion protein or pharmaceutical composition comprising the same is administered to a subject in a dose ranging from 0.2 mg to 2 mg. In another embodiment, the recombinant fusion protein or pharmaceutical composition comprising the same is administered to a subject in a dose ranging from 2 mg to 6 mg. In another embodiment, the recombinant fusion protein or pharmaceutical composition comprising the same is administered to a subject in a dose ranging from 4 mg to 10 mg. In another embodiment, the recombinant fusion protein or pharmaceutical composition comprising the same is administered to a subject in a dose ranging from 5 mg and 15 mg.

In one embodiment, a recombinant fusion protein or pharmaceutical composition comprising the same is administered to a subject in a dose ranging from 10 μg/kg-1000 μg/kg. In another embodiment, a recombinant fusion protein or pharmaceutical composition comprising the same is administered to a subject in a dose ranging from 25 μg/kg-600 μg/kg. In another embodiment, a recombinant fusion protein or pharmaceutical composition comprising the same is administered to a subject in a dose ranging from 50 μg/kg-400 μg/kg. In another embodiment, a recombinant fusion protein or pharmaceutical composition comprising the same is administered to a subject in a dose of about 25 μg/kg. In another embodiment, a recombinant fusion protein or pharmaceutical composition comprising the same is administered to a subject in a dose of about 50 μg/kg. In another embodiment, a recombinant fusion protein or pharmaceutical composition comprising the same is administered to a subject in a dose of about 100 μg/kg. In another embodiment, a recombinant fusion protein or pharmaceutical composition comprising the same is administered to a subject in a dose of about 200 μg/kg. In another embodiment, a recombinant fusion protein or pharmaceutical composition comprising the same is administered to a subject in a dose of about 300 μg/kg. In another embodiment, a recombinant fusion protein or pharmaceutical composition comprising the same is administered to a subject in a dose of about 400 μg/kg. In another embodiment, a recombinant fusion protein or pharmaceutical composition comprising the same is administered to a subject in a dose of about 500 µg/kg. In another embodiment, a recombinant fusion protein or pharmaceutical composition comprising the same is administered to a subject in a dose of about 600 µg/kg.

In one embodiment, a single one time dose of the recombinant fusion protein or pharmaceutical composition comprising the same is administered to a subject. In another embodiment, a total of two doses are administered to the subject. In another embodiment, a total of two or more doses are administered to the subject.

In another embodiment, a dose of the recombinant fusion protein or pharmaceutical composition comprising the same is administered to a subject at least once a day. In another embodiment, a dose of the recombinant fusion protein or pharmaceutical composition comprising the same is administered to a subject at least once every two days. In another embodiment, a dose of the recombinant fusion protein or pharmaceutical composition comprising the same is administered to a subject at least once a every two or more days. In another embodiment, a dose of the recombinant fusion protein or pharmaceutical composition comprising the same is administered to a subject every week, biweekly or every three weeks. In another embodiment, a dose of the recombinant fusion protein or pharmaceutical composition comprising the same is administered to a subject at least once a week. In another embodiment, a dose of the recombinant fusion protein or pharmaceutical composition comprising the same is administered to a subject at least once every two weeks. In another embodiment, a dose of the recombinant fusion protein or pharmaceutical composition comprising the same is administered to a subject at least once every three weeks. In another embodiment, a dose of the recombinant fusion protein or pharmaceutical composition comprising the same is administered to a subject at least once every three or more weeks. In another embodiment, a dose of the recombinant fusion protein or pharmaceutical composition comprising the same is administered to a subject two or more times a week. In another embodiment, a dose of the recombinant fusion protein or pharmaceutical composition comprising the same is administered to a subject two or more times a month. In another embodiment, a dose of the recombinant fusion protein or pharmaceutical composition comprising the same is administered to a subject two or more times a year. In another embodiment, a dose of the recombinant fusion protein or pharmaceutical composition comprising the same is administered to a subject two or more times every two years. In another embodiment, a dose of the recombinant fusion protein or pharmaceutical composition comprising the same is administered to a subject two or more times every two or more years.

In another embodiment, a dose of the recombinant fusion protein or pharmaceutical composition comprising the same is administered at least once every 36 hours. In another embodiment, a dose of the recombinant fusion protein or pharmaceutical composition comprising the same is administered at least once every 48 hours. In another embodiment, a dose of the recombinant fusion protein or pharmaceutical composition comprising the same is administered at least once every 60 hours. In another embodiment, a dose of the recombinant fusion protein or pharmaceutical composition comprising the same is administered at least once every 72 hours. In another embodiment, a dose of the recombinant fusion protein or pharmaceutical composition comprising the same is administered at least once every 84 hours. In another embodiment, a dose of the recombinant fusion protein or pharmaceutical composition comprising the same is administered at least once every 96 hours. In another embodiment, a dose of the recombinant fusion protein or pharmaceutical composition comprising the same is administered at least once every 5 days. In another embodiment, a dose of the recombinant fusion protein or pharmaceutical composition comprising the same is administered at least once every 6 days. In another embodiment, a dose of the recombinant fusion protein or pharmaceutical composition comprising the same is administered at least once every 7 days. In another embodiment, a dose of the recombinant fusion protein or pharmaceutical composition comprising the same is administered at least once every 8-10 days. In another embodiment, a dose of the recombinant fusion protein or pharmaceutical composition comprising the same is administered at least once every 10-12 days. In another embodiment, a dose of the recombinant fusion protein or pharmaceutical composition comprising the same is administered at least once every 12-15 days. In another embodiment, a dose of the recombinant fusion protein or pharmaceutical composition comprising the same is administered at least once every 15-25 days. In another embodiment, a dose of the recombinant fusion protein or pharmaceutical composition comprising the same is administered at least once every 20-30 days.

In one embodiment, a dose of the recombinant fusion protein or pharmaceutical composition comprising the same is administered to a subject at least once every 1 month. In one embodiment, a dose of the recombinant fusion protein or pharmaceutical composition comprising the same is administered at least once every 2 months. In one embodiment, a dose of the recombinant fusion protein or pharmaceutical composition comprising the same is administered at least once every 3 months. In one embodiment, a dose of the recombinant fusion protein or pharmaceutical composition comprising the same is administered at least once every 4 months. In one embodiment, a dose of the recombinant fusion protein or pharmaceutical composition comprising the same is administered at least once every 5 months. In one embodiment, a dose of the recombinant fusion protein or pharmaceutical composition comprising the same is administered at least once every 6 months. In one embodiment, a dose of the recombinant fusion protein or pharmaceutical composition comprising the same is administered at least once every 6-12 months. In another embodiment, a dose of the recombinant fusion protein or pharmaceutical composition comprising the same is administered quarterly. In another embodiment, the dose is administered daily, weekly, biweekly, monthly or annually. In another embodiment, the dose is administered once, twice, or two or more times a day, a week, a month or a year. In another embodiment, the dose is administered every two, three, four, or at least five years.

In one embodiment, repeat administrations (doses) of compositions of this invention may be undertaken immediately following the first course of treatment or after an interval of days, weeks, or years to achieve the desired effect as further provided herein (e.g. to prevent or treat cardiovascular disease or condition, or a CNS-related disease or condition).

In one embodiment, the pharmaceutical compositions are administered by intravenous, intra-arterial, subcutaneous or intramuscular injection of a liquid preparation. In another embodiment, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration.

In some embodiments, compositions for use in the methods disclosed herein comprise solutions or emulsions, which in some embodiments are aqueous solutions or emulsions comprising a safe and effective amount of the compounds disclosed herein and optionally, other compounds, intended for intravenous or subcutaneous administration.

In some embodiments, the various constituents of the compositions come pre-measured and/or prepackaged and/or ready for use without additional measurement, etc. The present invention also optionally comprises kits for conducting/using the methods and/or the compositions of the invention. In particular, these kits optionally include, e.g., appropriate recombinant fusion protein (and optionally mixtures of a number of such proteins for performing synergistic treatments, see, above), and optionally appropriate disease related antigen(s) as well). Additionally, such kits can also comprise appropriate excipients (e.g., pharmaceutically acceptable excipients) for performing therapeutic and/or prophylactic treatments of the invention. Such kits optionally contain additional components for the assembly and/or use of the compositions of the invention including, but not limited to, e.g., diluents, etc.

The compositions described herein are optionally packaged to include all (or almost all) necessary components for performing the methods of the invention or for using the compositions of the invention (optionally including, e.g., written instructions for the use of the methods/compositions of the invention). For example, the kits can optionally include such components as, e.g., buffers, reagents, serum proteins, antibodies, substrates, etc. In the case of prepackaged reagents, the kits optionally include pre-measured or pre-dosed amounts that are ready to incorporate into the methods without measurement, e.g., pre-measured fluid aliquots, or pre-weighed or pre-measured solid reagents that can be easily reconstituted by the end-user of the kit.

Such kits also typically include appropriate instructions for performing the methods of the invention and/or using the compositions of the invention. In some embodiments, the components of the kits/packages are provided in a stabilized form, so as to prevent degradation or other loss during prolonged storage, e.g., from leakage. A number of stabilizing processes/agents are widely used for reagents, etc. that are to be stored, such as the inclusion of chemical stabilizers (i.e., enzymatic inhibitors, microbicides/bacteriostats, anticoagulants), etc. Actual dosage levels of the active ingredients in the pharmaceutical compositions of the present invention may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors well known in the medical arts.

The composition must be sterile and fluid to the extent that the composition is deliverable by syringe. In addition to water, the carrier preferably is an isotonic buffered saline solution. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Actual dosage levels of the active ingredients in the pharmaceutical compositions of the present invention may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors well known in the medical arts.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements 5 other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The present invention further provides a kit for preventing, treating or delaying a cardiovascular disease or condition in a human, wherein the kit comprises one or more doses of pharmaceutical composition comprising a recombinant fusion protein disclosed herein used for preventing, treating or delaying a cardiovascular disease or condition, and instructions on how to use the pharmaceutical preparation or composition.

The present invention further provides a kit for preventing, treating or delaying a CNS-related disease or condition in a human, wherein the kit comprises one or more doses of pharmaceutical composition comprising a recombinant fusion protein disclosed herein used for preventing, treating or delaying a cardiovascular disease or condition, and instructions on how to use the pharmaceutical preparation or composition.

The present invention further provides a kit for preventing, treating or delaying heart failure with preserved ejection fraction in a human, wherein the kit comprises one or more doses of pharmaceutical composition comprising a recombinant fusion protein disclosed herein used for preventing, treating or delaying heart failure with preserved ejection fraction, and instructions on how to use the pharmaceutical preparation or composition.

The following examples are presented in order to more fully illustrate the preferred embodiments of the invention. They should in no way be construed, however, as limiting the broad scope of the invention.

EXAMPLES

Example 1—Cloning and Construction of Expression Plasmids

DNA sequences encoding the recombinant fusion proteins' heavy chain (named NPCFA and NPCF for the sequences with or without Fc mutations, respectively) and light chain (named PAL) were synthesized by GENEWIZ (Suzhou, China). Expression vector pCHOGUN was obtained from Horizon Discovery (Cambridge, UK) under a licensing agreement. Construction of the expression plasmids is carried out as outlined in FIG. 1. Briefly, pCHOGUN vector was linearized by restriction enzyme BfuAI and gene insert fragments such as NPCF, NPCFA, and PAL were purified following double restriction enzyme digestion by NcoI and AscI. The linearized pCHOGUN/BfuAI and the purified gene insert fragment were ligated per standard protocol and then transformed into E. coli DH5α competent cells. DH5α cells were plated and incubated overnight at 37° C. Plasmids pCHOGUN-NPCF, pCHOGUN-NPCFA and pCHOGUN-PAL were isolated and confirmed by restriction enzyme digestion or PCR. The plasmid containing the heavy chain insert (pCHOGUN-NPCF or pCHOGUN-NPCFA) was digested with restriction enzymes BspEI and PciI, whereas the plasmid containing the light chain insert (pCHOGUN-PAL) was digested with restriction enzymes NgoMIV and PciI. Following the restriction enzyme digestion, the fragments with the heavy or light chain insert were purified, ligated and then transformed into DH5α cells. The plasmid constructs containing both the heavy and light chain inserts (pCHOGUN-NPCF+PAL or pCHOGUN-NPCFA+PAL) were identified and confirmed by restriction enzyme digestion and DNA sequencing.

Example 2—Antibody Production, Purification and Characterization

HD-BIOP3, a glutamine synthetase-null ($GS^{-/-}$) cell line derived from CHO K1 cells, was obtained from Horizon Discovery (Cambridge, UK) under a licensing agreement. Plasmid DNA is isolated using commercially available Qiagen Plasmid Kits. Transfection of the plasmid DNA into HD-BIOP3 cells was performed using a commercially available electroporation system from Lonza. The transfected cells were plated in 96-well plates and underwent pool selection using standard procedures. Cells from the selected pools were cultured in 125-mL shake flasks for 10-14 days and the media were harvested for antibody purification. Antibody proteins were purified by protein-A affinity chromatography followed by size-exclusion chromatography and then analyzed with SDS-PAGE and Western blot according to standard protocols.

Figure 2A:
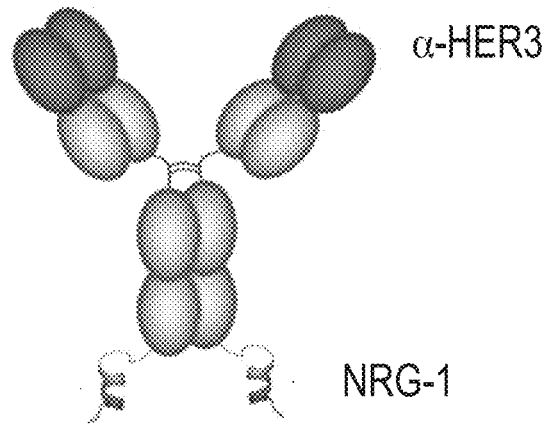
FIGS. 2A-2D illustrate the schematic structure of the recombinant fusion protein disclosed herein.
Figure 2B:
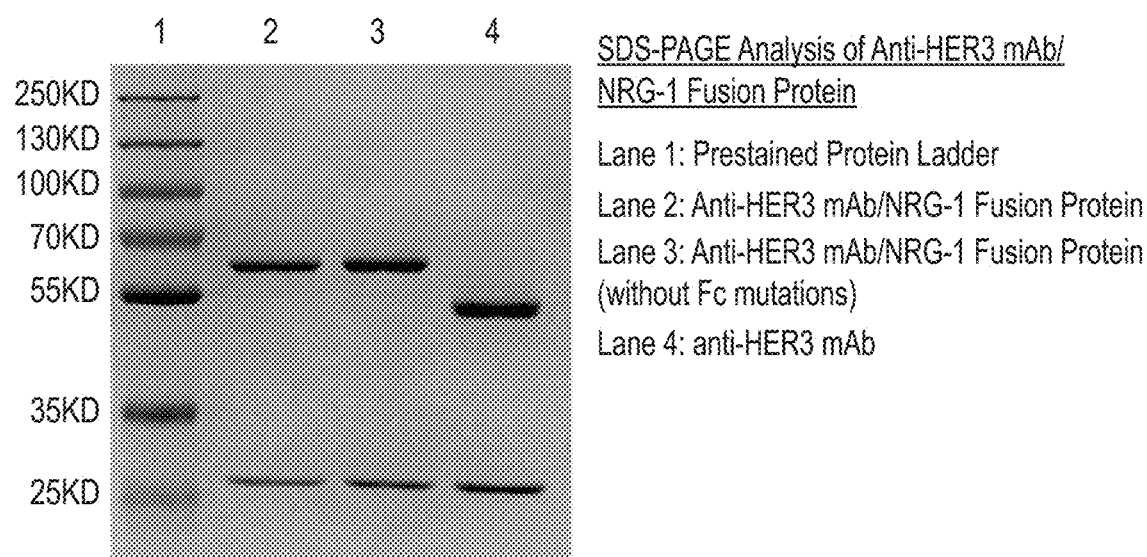
Figure 2C:
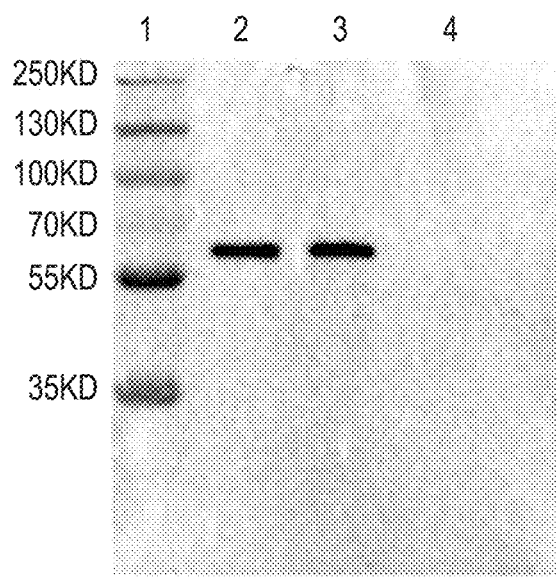
Figure 2D:
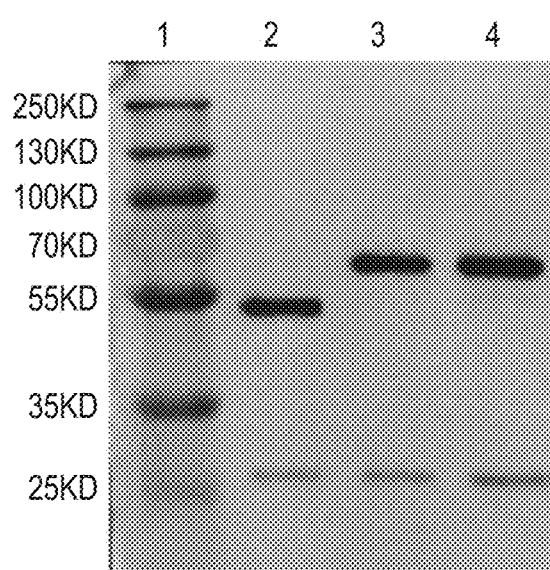

FIG. 2A illustrates the schematic structure of the recombinant fusion protein disclosed herein. FIG. 2B shows representative data generated by SDS-PAGE analysis. Western blot results detected by primary antibody specific for the 61-amino acid active fragment of NRG-1 comprising the HER3/4 binding domain ("NRG-1", R&D Systems, Minneapolis, Minn.) or IgG are shown in FIGS. 2C and 2D, respectively.

Example 3—Molecular Integrity Assessed by SPR-Based Binding Assay

Molecular structure integrity of the recombinant fusion protein disclosed herein is assessed by evaluating its concurrent binding ability to HER3 protein and Anti-NRG-1 antibody. His-tagged HER3 recombinant protein (Sino Biological, Beijing, China) was captured on the sensor chip immobilized with anti-His antibody (Thermo Fisher, Waltham, Mass.) (Step 1), followed by the injection of samples (including the recombinant fusion protein disclosed herein, the recombinant fusion protein disclosed herein without Fc mutations, anti-HER3 mAb (Step 2), and anti-NRG-1 antibody (R&D Systems, Minneapolis, Minn.) (Step 3). The attachment of His-HER3 on the sensor chip can be visualized through the increase of signal on all 6 channels in step 1. Both the recombinant fusion protein disclosed herein and the recombinant fusion protein disclosed herein without Fc mutations generated significant response on step 2 by binding to HER3 and on step 3 by binding to injected anti-NRG-1 antibody (Ch1, 3), indicating the presence of HER3-binding epitope and NRG-1 on the recombinant fusion protein disclosed herein. In contrast, the anti-HER3 mAb bound only to His-HER3 on step 2, but not Anti-NRG-1 antibody and buffer (Step 3) (Ch 4, 5), verifying the absence of NRG-1-binding activity for the anti-HER3 mAb molecule. Buffer was injected at Step 2 and 3 as blank control. Therefore, both the HER3-binding epitope and NRG-1 are present in the recombinant fusion protein of the invention.

Figure 3:
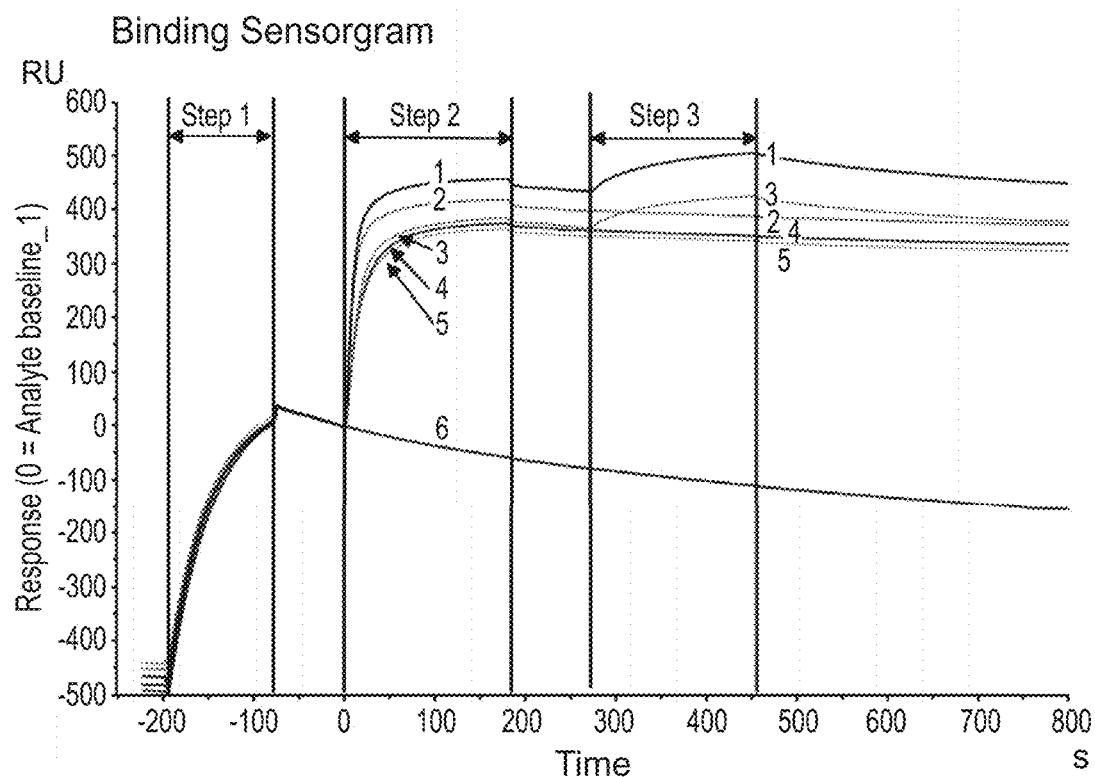
FIG. 3 illustrates a binding analysis showing that the recombinant fusion protein disclosed herein binds to HER3 protein (Curve 1, Step 2) and can simultaneously bind an anti-NRG-1 antibody (Curve 1, Step 3). Note that Fc mutations were introduced into the recombinant fusion protein disclosed herein to knock out the Fc effector function of the parent antibody sequence encoding a HER3 specific antibody, which may mitigate the undesired cytotoxicity towards normal tissues expressing HER3 receptor.
Figure 4A:
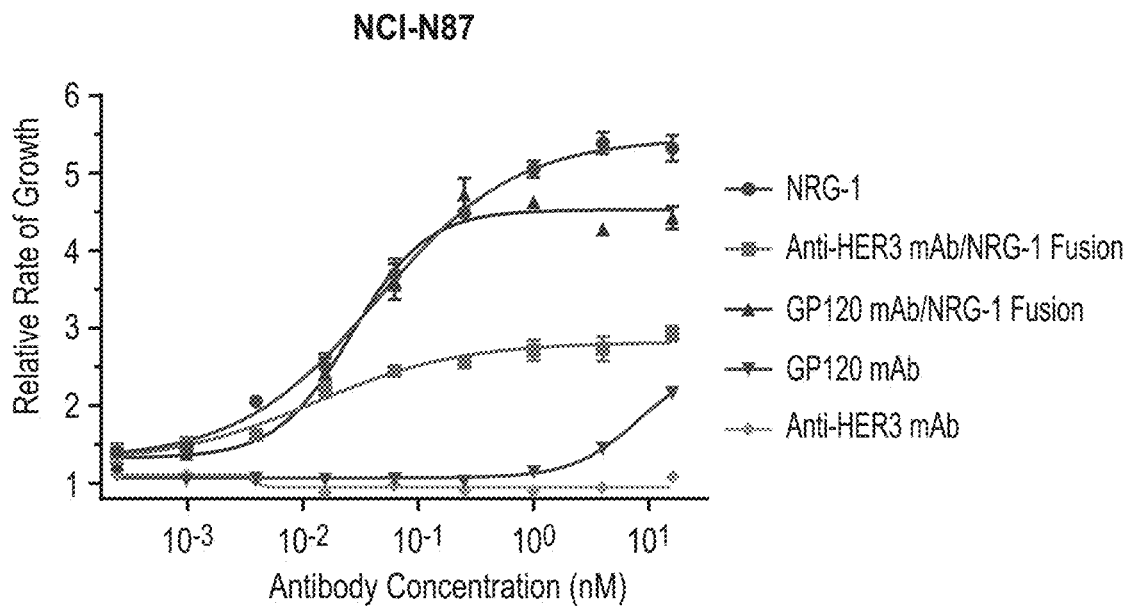
FIGS. 4A-4D show representative graphs showing the mean relative growth rate±SEM (n=3) for different cancer cell lines treated with an anti-HER3 mAb/NRG-1 fusion protein or controls.
Figure 4B:
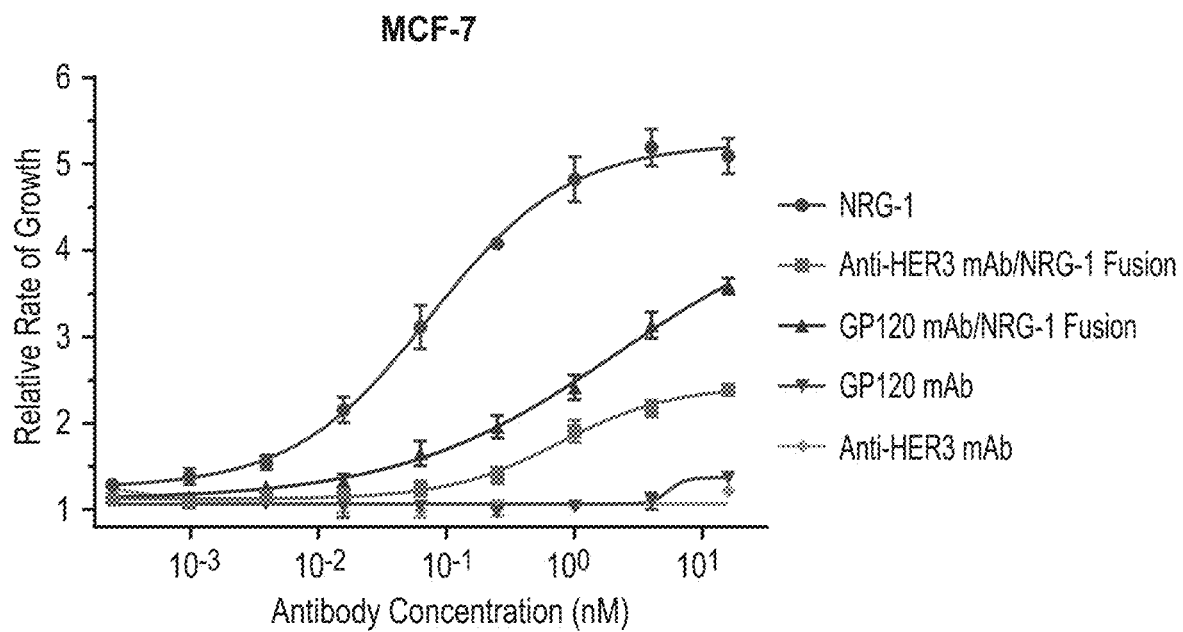
Figure 4C:
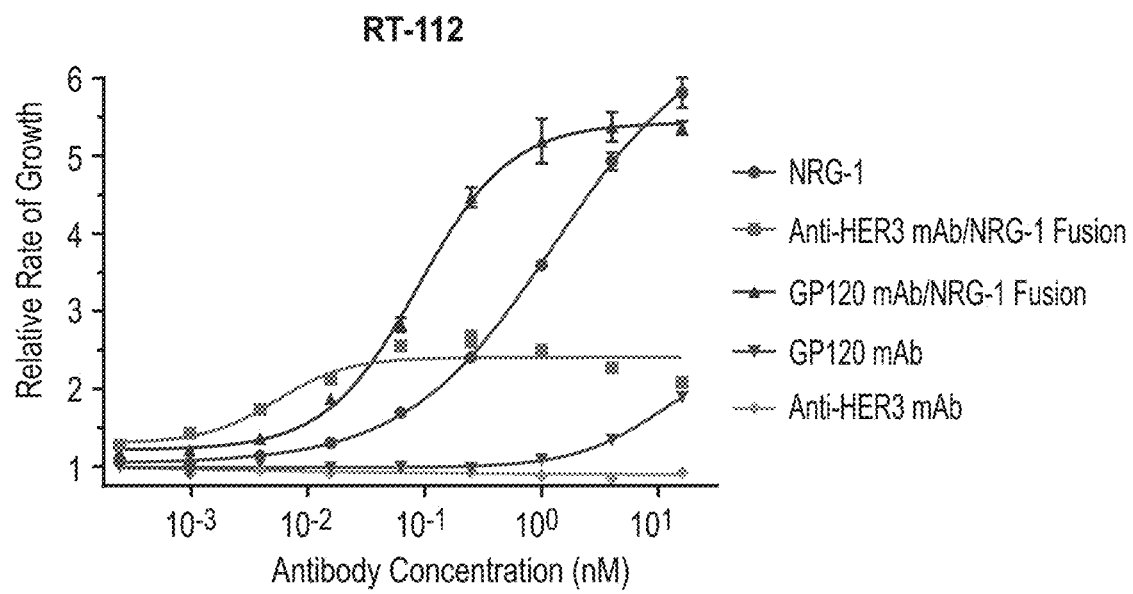
Figure 4D:
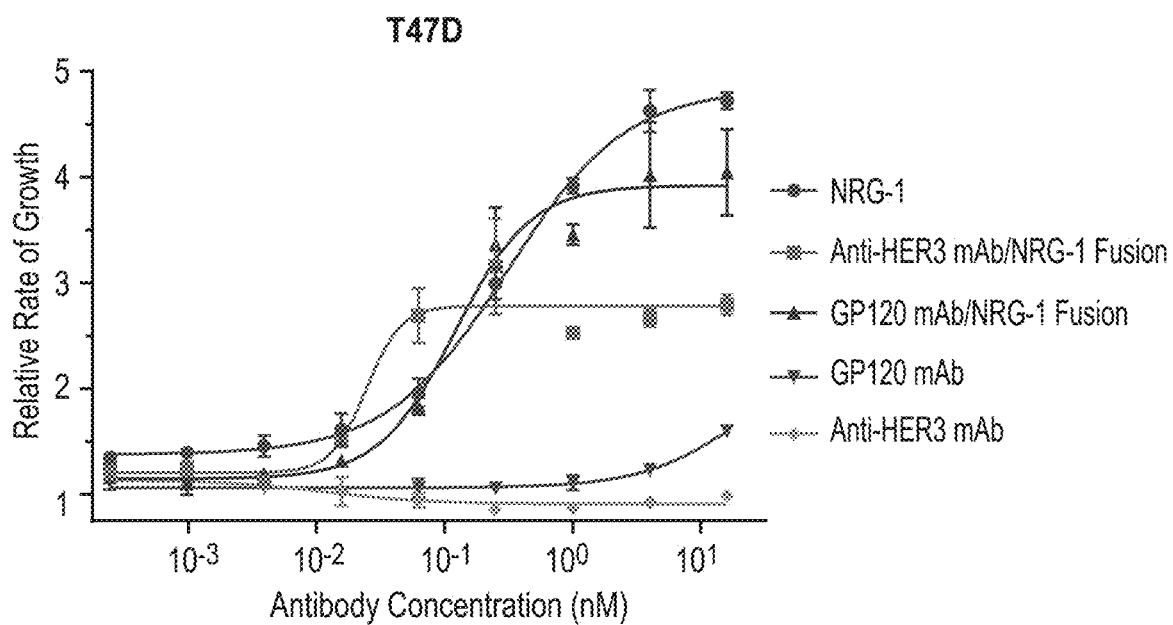

The binding sensorgram and sample injection sequences are shown in FIG. 3.

Example 4—Effect on Tumor Cell Line Proliferation In Vitro

Tumor cells were seeded in 96-well plates at 2,500-20,000 cells per well, depending on the growth kinetics of each cell line. Cells were then treated with the recombinant fusion protein disclosed herein, antibody or control protein in a step-wise 1:4 serial dilution series for 5 days. Cell viability was assessed using Cell Counting Kit-8 from Dojindo Molecular Technologies (Kumamoto, Japan) according to the manufacturer's instructions. Data were analyzed with GraphPad Prism software and are presented as the rate of growth relative to the untreated control.

FIG. 4 includes representative graphs showing the mean relative growth rate±SEM (n=3) for different cancer cell lines: (A) NCI-N87, gastric; (B) MCF-7, breast; (C) RT-112, bladder; and (D) T47D, breast. Compared to the control NRG-1 and GP120 mAb/NRG-1 fusion proteins, the recombinant fusion protein disclosed herein demonstrates markedly lower activity in promoting cancer cell proliferation.

Example 5—Activation of PI3K/AKT Signaling Pathway in Human Cardiomyocytes

Human cardiomyocytes obtained from Cellular Dynamics (Madison, Wis.) were seeded in 0.1% gelatin-coated 96-well plates and recovered in the plating medium (Cellular Dynamics) for 4 hours. Cells were then cultured in the maintaining medium (Cellular Dynamics) for 96 hours before used for experimentation. To examine the ability of the recombinant fusion protein of the invention to activate the HER2:HER4 signaling pathway in cardiomyocytes, cells were first starved for 4 hours in serum-free media and then treated with the recombinant fusion protein or control agents (NRG-1, GP120 mAb/NRG-1, anti-HER3 mAb, or GP120 mAb) in a step-wise 1:4 serial dilution series for 15 minutes. At the end of treatment, cells were lysed and analyzed for AKT phosphorylation using Abcam's Phospho-AKT/Total AKT ELISA Kit (Cambridge, Mass.) following the manufacturer's instructions. Data were analyzed with GraphPad Prism software and are presented as the ratio of phospho-AKT to total AKT relative to the untreated control.

For western blot analysis, cells were seeded in 6-well plates and treated with the recombinant fusion protein of the invention or control agents at a single concentration of 16 nM. At the end of treatment, cells were lysed in RIPA lysis buffer containing protease and phosphatase inhibitors. SDS-PAGE and Western blot were conducted per standard protocols. The total AKT and phosphor-AKT were blotted with AKT rabbit antibody and p-AKT(S473) rabbit antibody (Cell Signaling; Danvers, Mass.), respectively.

Figure 5A:
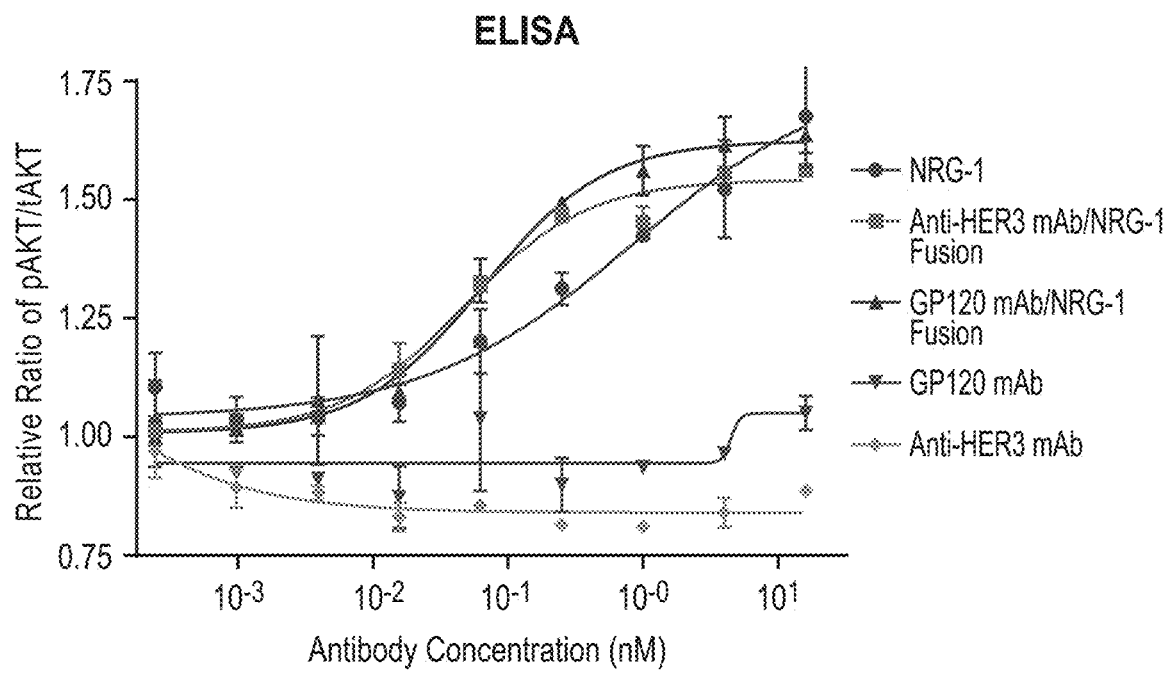
FIGS. 5A-5B illustrate that despite reduced cancer cell growth potential, the recombinant fusion protein provided herein fully preserves the ability to induce PI3K/AKT signaling in cardiomyocytes—demonstrating comparable activity to recombinant NRG-1 and GP120 mAb/NRG-1 fusion protein.
Figure 5B:
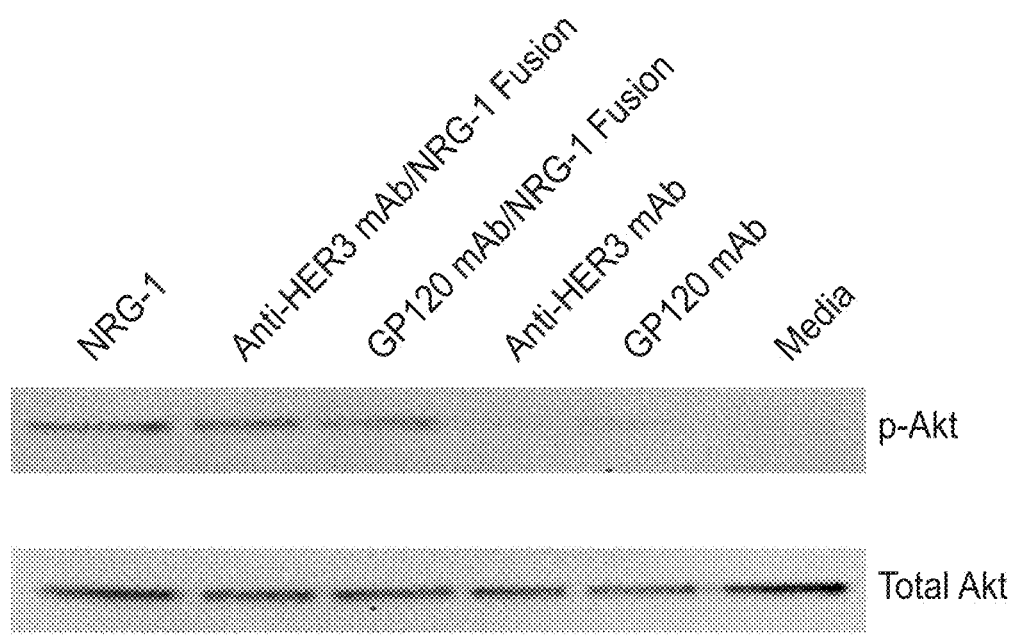

FIGS. 5A-5B show AKT phosphorylation in response to stimuli in human cardiomyocytes. Results suggest that the recombinant fusion protein disclosed herein can activate the HER2:HER4 signaling pathway in cardiomyocytes with a potency comparable to NRG-1.

Example 6—Induction of HER2:HER3 Dimerization and HER2:HER4 Dimerization

Figure 6A:
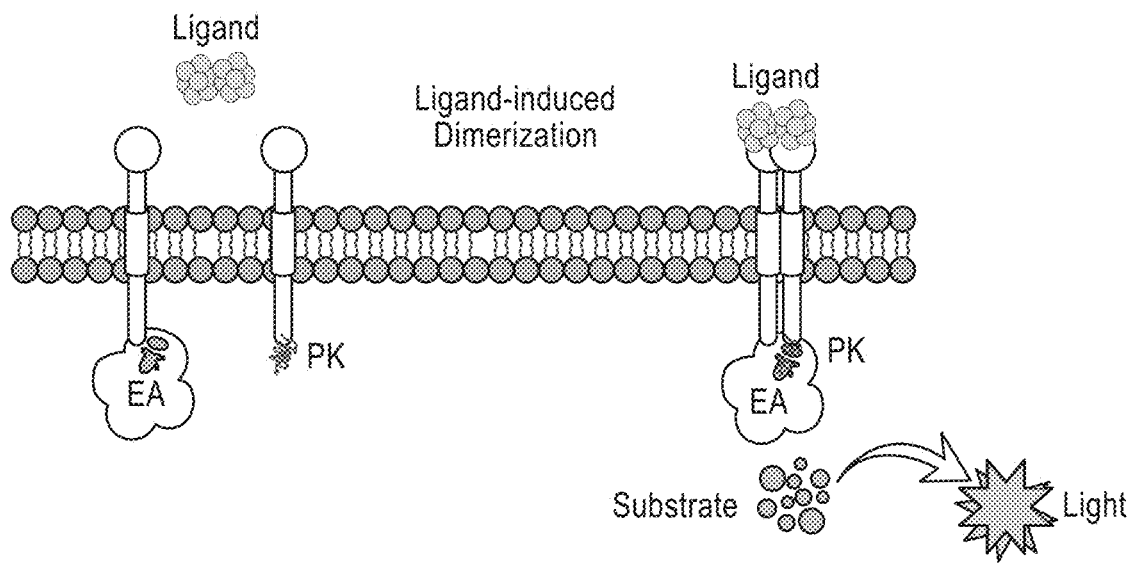
FIGS. 6A-6C show direct comparison of HER2/4 and HER2/3 dimerization in the presence of the recombinant fusion protein disclosed herein and controls.

PathHunter Dimerization Assay developed by Eurofins DiscoverX (Fremont, Calif.) detects ligand induced dimerization of two subunits of a receptor-dimer pair. The assay principle is illustrated in FIG. 6A. β-gal enzyme is split into two fragments, ProLink (PK) and enzyme receptor (EA). The cells have been engineered to co-express target protein 1 fused to enzyme donor PK, and target protein 2 fused to enzyme acceptor EA. Binding of ligand to one target protein induces it to interact with the other target protein, forcing complementation of the two enzyme fragments and resulting in the enzyme reaction to release chemiluminescent signal which is detected as Relative Fluorescence Unit or RFU.

PathHunter U2OS ErbB2/ErbB4 dimerization cell line and ErbB2/ErbB3 dimerization cell line were obtained from Eurofins DiscoverX. Cells were seeded at 4,000 cells/well in 384-well plates and incubated at 37° C./5% $CO_2$ overnight. Testing agents were prepared in a step-wise 1:4 serial dilution series starting from 28.8 nM, and then added to cells in 384-well plates. After 4 hours of incubation, cells were assayed for receptor dimerization according to the manufacturer's instructions. Data were analyzed with GraphPad Prism software and are presented as mean RFU±SEM (n=3).

Figure 6B:
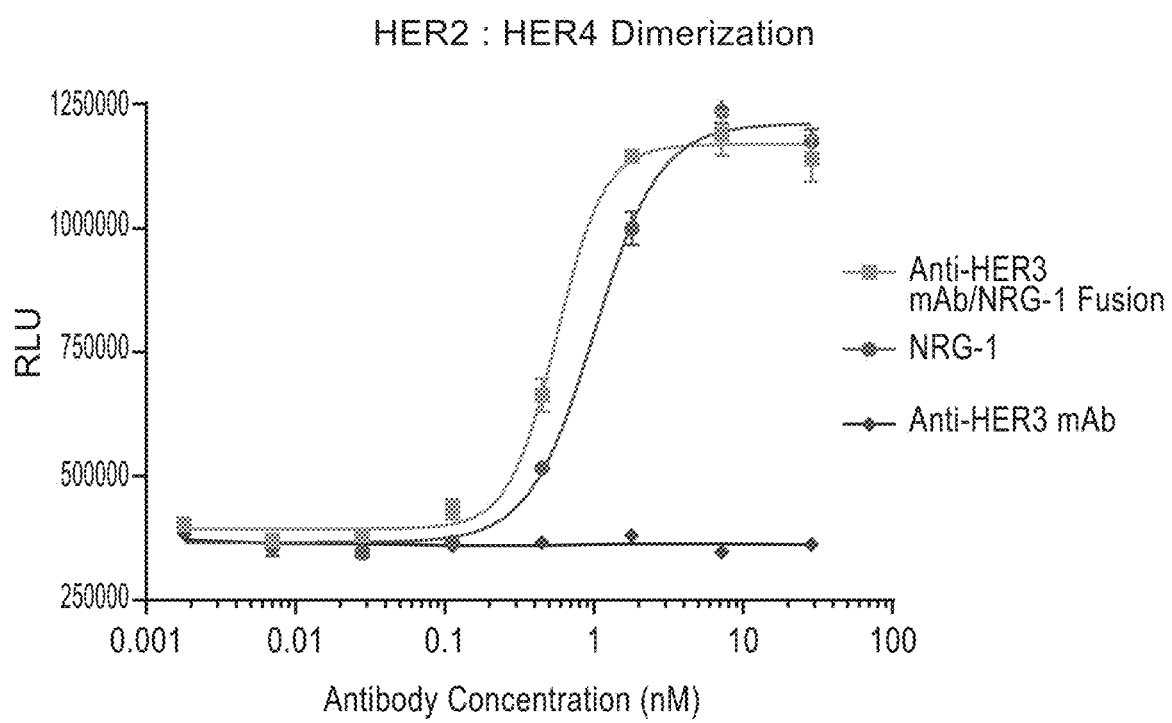
Figure 6C:
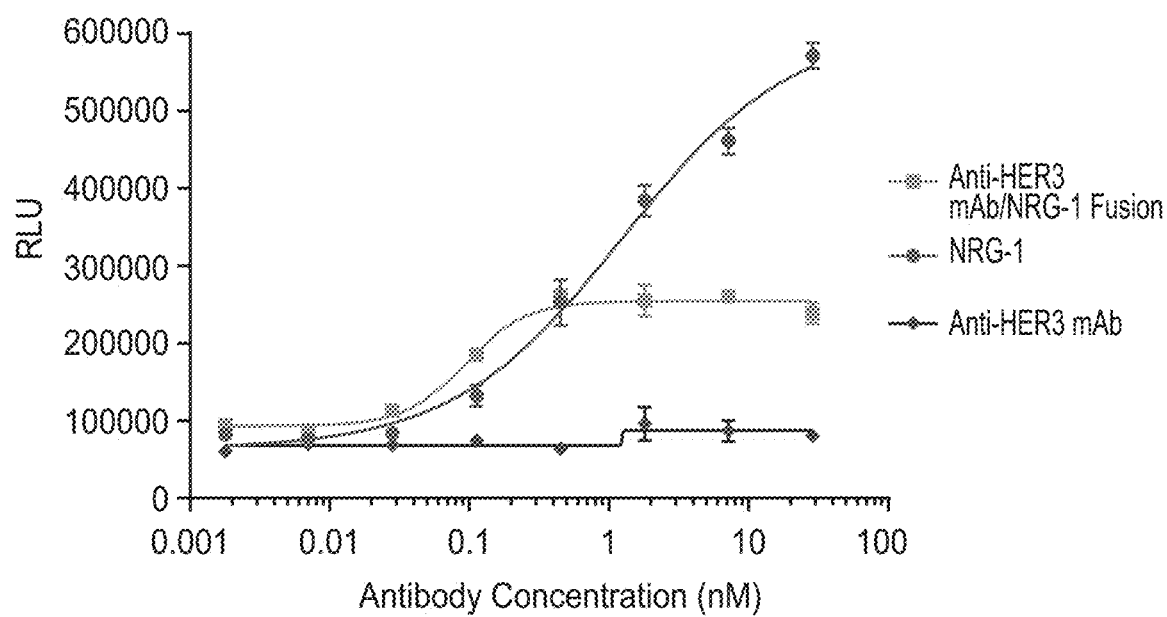
Figure 7:
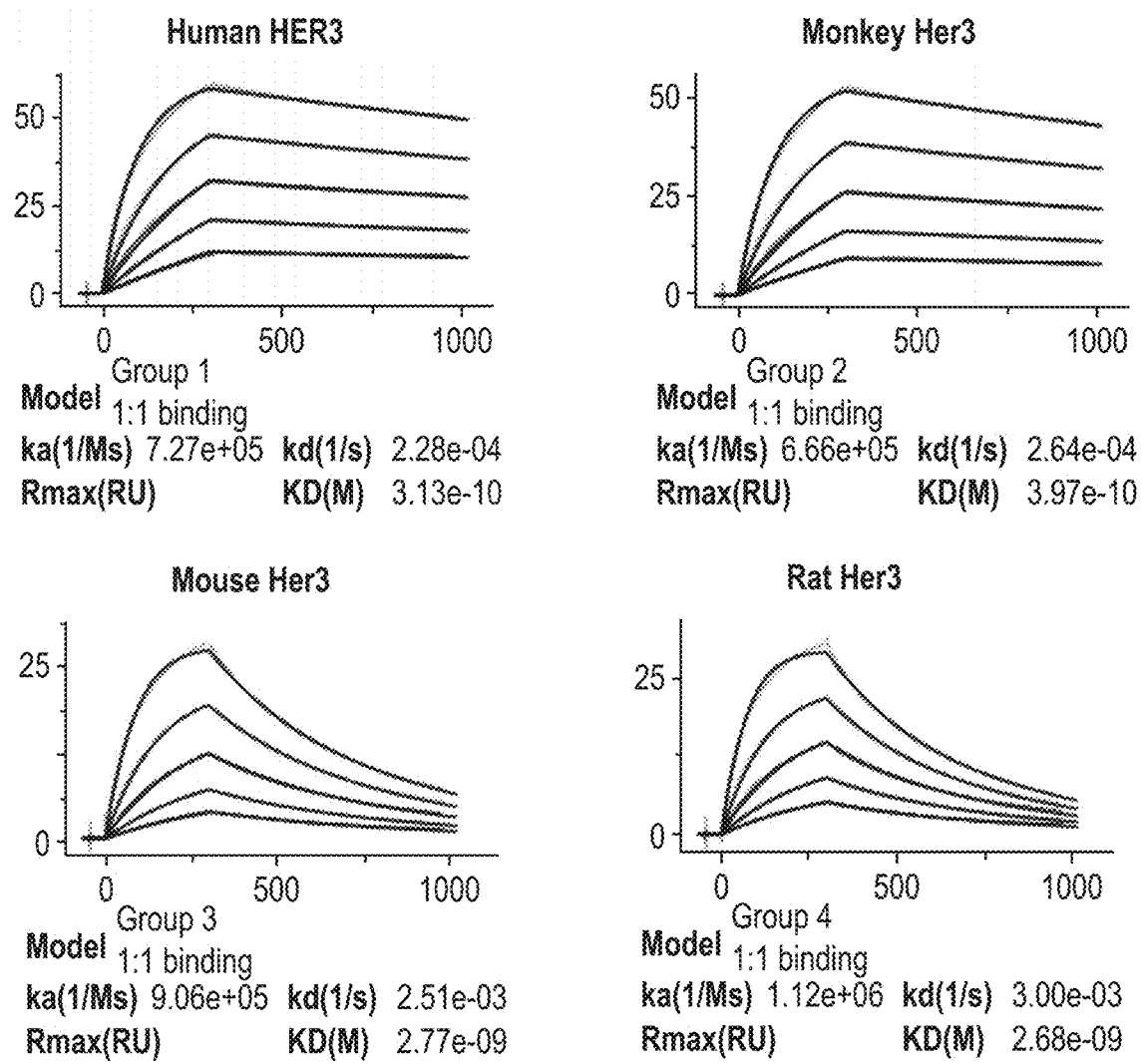
FIG. 7 illustrates the binding affinity of anti-HER3 mAb/NRG-1 fusion protein of the invention to HER3 antigen across different species including human, monkey, rat and mouse. The equilibrium dissociation rate (KD) determined by BIAcore analysis is $3.13 \times 10^{-10}$ (human), $3.97 \times 10^{-10}$ (monkey), $2.68 \times 10^{-9}$ (rat) and $2.77 \times 10^{-9}$ (mouse), respectively. These data indicate that the recombinant fusion protein of the invention has a similar binding affinity to human and monkey HER3, whereas its affinity to rodent (rat and mouse) HER3 is lower by approximately one order of magnitude.

As shown in FIGS. 6B and 6C, the recombinant fusion protein disclosed herein can induce HER2/HER4 dimerization with potency comparable to NRG-1; whereas its ability to induce HER2/HER3 dimerization is much weaker. As negative controls for the study, neither the isotype control antibody GP120 mAb nor the anti-HER3 mAb induced receptor dimerization.

Having described embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

Example 7—In Vivo Efficacy of the Recombinant Fusion Protein in a Rat Model of Systolic Heart Failure To evaluate the ability of the recombinant fusion protein to regenerate cardiac function in a disease model, a Sprague Dawley rat model of myocardial infarction and systolic heart failure was employed. To establish the disease model, a 6-0 silk suture was used to ligate the left anterior descending coronary artery (LAD) 3-4 mm below the left atrial appendage in a surgical procedure. Four weeks following ligation, the ejection fraction (EF) was recorded by M-mode echocardiography (ECG) Doppler ultrasound to measure cardiac function against the baseline EF prior to surgery. A threshold of minimum 30% decrease of EF was used for inclusion in the subsequent study. Sham control animals underwent an identical surgery without the LAD ligation.

After establishing the disease model, animals were divided into five groups of eleven rats each, with an additional ten sham-surgery rats included in a sixth group. The study was designed for each group to receive twice-weekly tail vein injections for a period of four weeks, or eight total injections. Both the sham surgery group and the negative control of vehicle group received saline, three groups received the recombinant fusion protein at 1, 3, or 10 mg/kg, and the final group received a positive control of GP120 mAb/NRG-1 fusion protein (10 mg/kg).

Due to the body-weight loss observed during the study, treatment was discontinued prior to the full sequence of eight injections in the recombinant fusion protein groups receiving 3 mg/kg and 10 mg/kg, with those groups receiving only six and three injections respectively. All other groups received the full set of eight injections.

Figure 8:
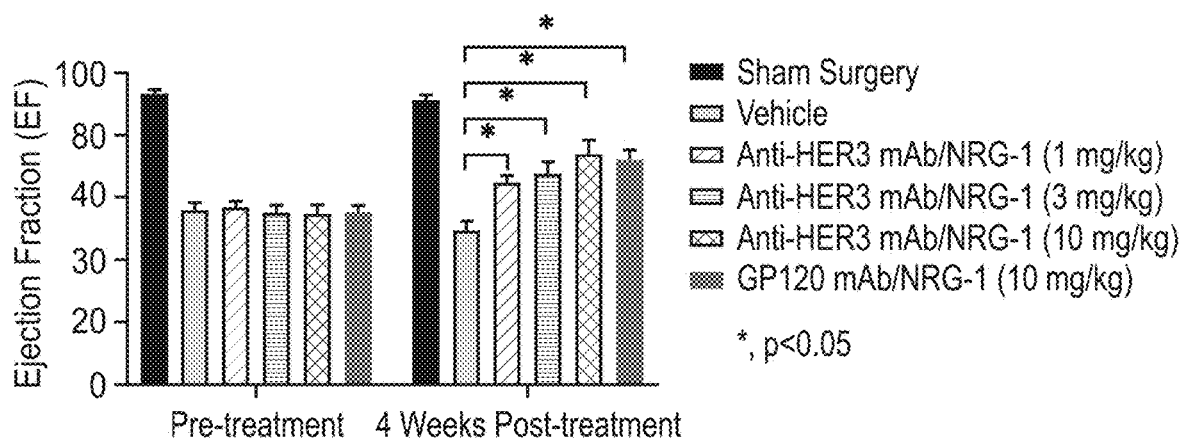
FIG. 8 is a plot that illustrates the effect of the recombinant fusion protein on ejection fraction (EF) in rat model of systolic heart failure induced by coronary artery ligation.

Four weeks following the first treatment, EF was again measured by M-mode ECG. As shown in FIG. 8, relative to baseline the recombinant fusion protein significantly increased the EF in all three dose groups. Specifically, increases of 14.7% (P<0.001), 26.9% (P<0.001), and 36.6% (P<0.001) were observed for the 1, 3, and 10 mg/kg groups respectively. The GP120 mAb/NRG-1 positive control increased EF by 28.8% (P<0.001) at the matched time point. Saline showed no effect in either the sham control group or the vehicle control group.

Figure 9:
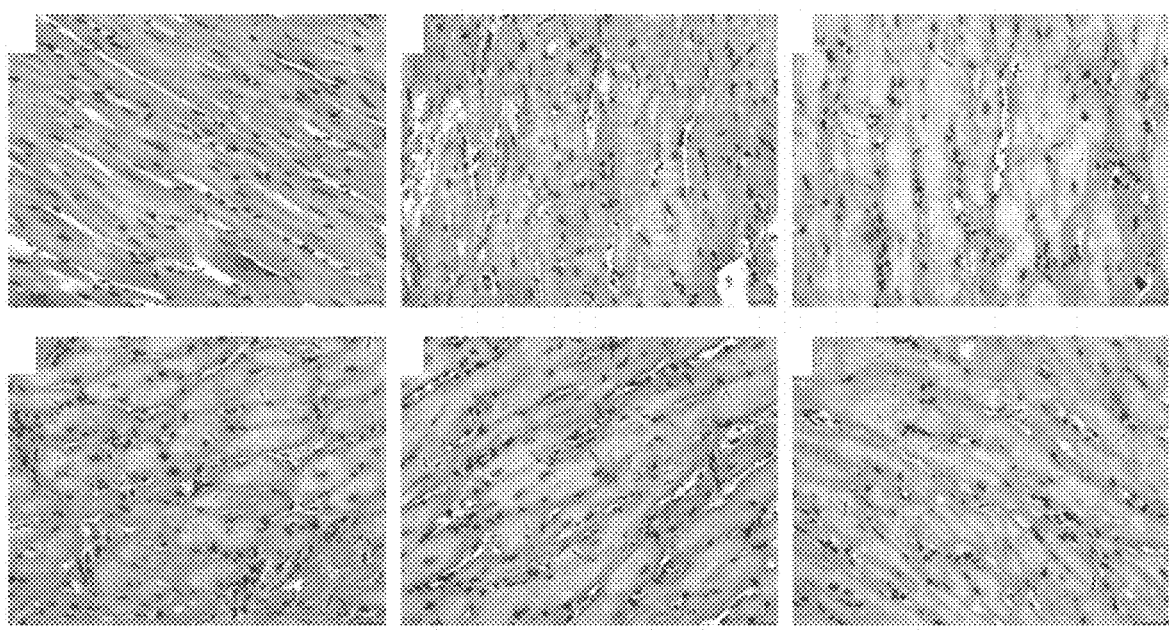
FIG. 9 is a series of 6 images that show histopathological changes in cardiac muscle structure in a rat model of systolic heart failure induced by coronary artery ligation. Cardiac tissues next to the surgical site were collected and fixed in 4% formaldehyde, paraffin sections were then prepared and stained with H&E. The top left image shows cardiac tissue from a sham surgery control rat. The top middle image shows cardiac tissue from a systolic heart failure model rat treated with vehicle control. The top right image shows cardiac tissue from a systolic heart failure model rat treated with GP120 mAb/NRG-1 (10 mg/kg). The bottom left image shows cardiac tissue from a systolic heart failure model rat treated with anti-HER3 mAb/NRG-1 (1 mg/kg). The bottom middle image shows cardiac tissue from a systolic heart failure model rat treated with anti-HER3 mAb/NRG-1 (3 mg/kg). The bottom right image shows cardiac tissue from a systolic heart failure model rat treated with anti-HER3 mAb/NRG-1 (10 mg/kg).

Following the collection of ECG values at 28 days post-treatment, mice were euthanized and the cardiac tissues next to the surgical site were collected, fixed in 4% formaldehyde, and embedded in paraffin. Five μm thick paraffin sections of the heart tissues were stained with hematoxylin and eosin dyes, and histopathological changes were observed under a light microscope. As shown in FIG. 9, in the sham operation group, the cardiomyocytes were arranged in an orderly fashion and the cytoplasm and the myocardial fibers were evenly stained. No inflammatory cell infiltration was observed in the interstitial spaces and no myocardial necrosis was found. In contrast, in the vehicle control group, the myocardial infarction marginal zone exhibited widened gaps between myocardial cells; the nuclei were condensed and shattered and the myocardial fiber arrangement lost its ordered structure; the cell size was enlarged and the interstitial edema was noticed. Treatment with the recombinant fusion protein partially alleviated the pathological changes in the myocardial infarction zone, including significant reduction of necrotic cells, narrowed interstitial spaces between myocardial cells, and recovery of myocardial fiber arrangement towards normal structure.

Example 8—The Recombinant Fusion Protein Attenuated Tumor Growth in Subcutaneous FaDu Carcinoma Xenograft Model in NOD/SCID Mice To evaluate the potential risk of the recombinant fusion protein in promoting tumor growth, an in vivo study in a FaDu carcinoma xenograft model was carried out. NOD/SCID mice (Beijing AK Bio-Technology Co. Ltd.) were maintained in SPF facility at the CrownBio international R&D center (Beijing, China) in accordance with institutional guidelines. All experiments were performed in accordance with the requirements of the Association for Assessment and Accreditation of Laboratory Animal Care (AAALAC) and with the permission of the CrownBio IACUC Committee.

Female NOD/SCID mice, age 7-10 weeks, were inoculated subcutaneously in the right flank with FaDu tumor cells ($3 \times 10^6$) suspended in 0.1 ml of PBS. When tumors reached approximately 150 mm$^3$, mice were randomized and sorted into 6 study groups with 8 animals per group. Test samples were administrated intravenously by tail vein injection twice a week for three consecutive weeks, for a total of 6 treatments. Tumor growth was monitored by caliper measurements. The study was terminated at 21 days post-treatment.

Figure 10:
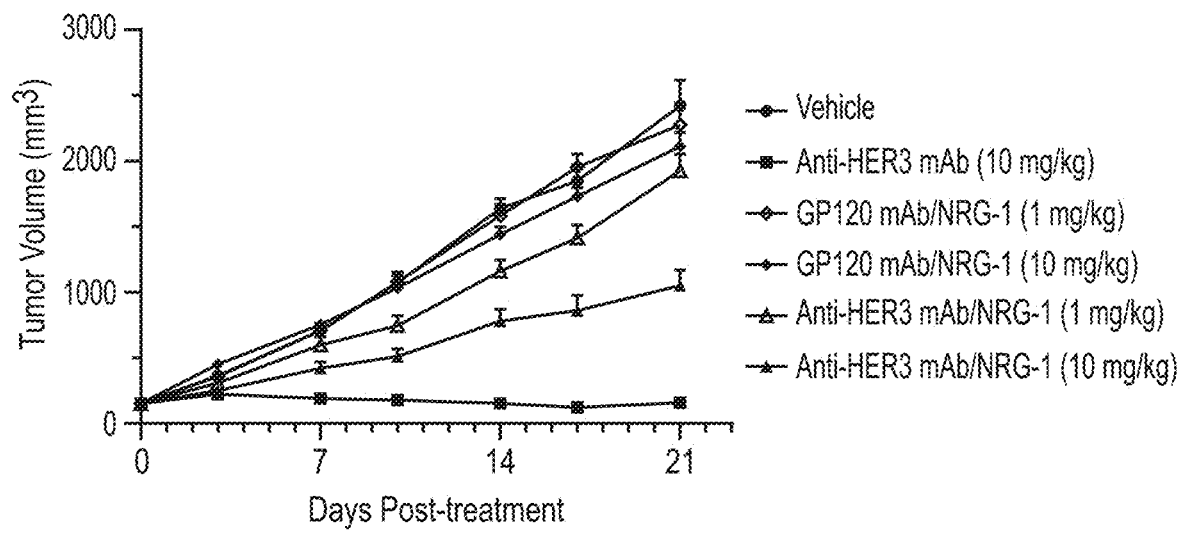
FIG. 10 is a graph illustrating the evaluation of in vivo anti-tumor activity using a subcutaneous FaDu carcinoma xenograft model in NOD/SCID mice.
Figure 11:
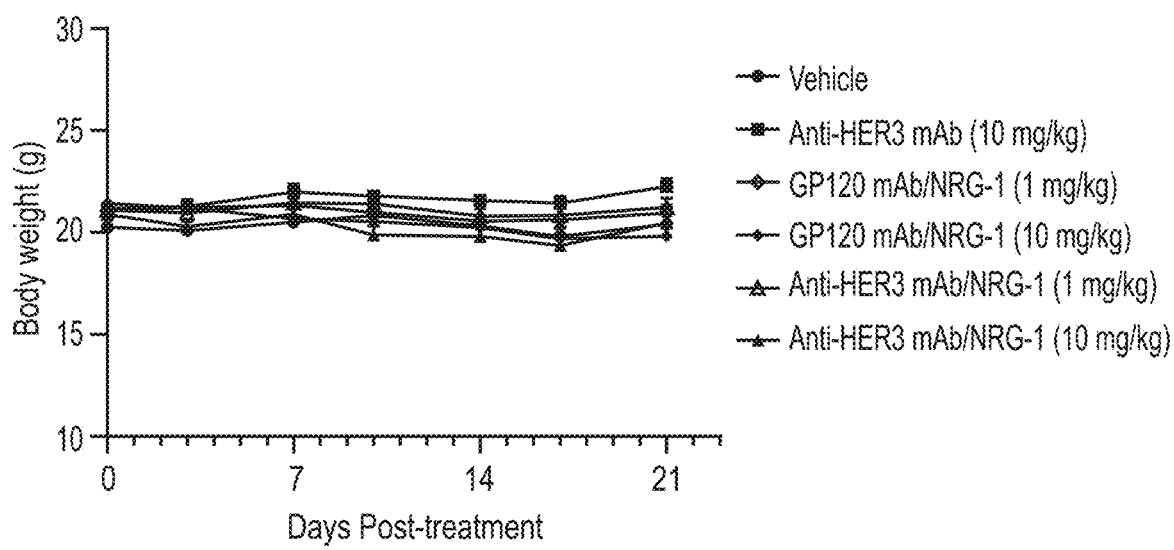
FIG. 11 is a graph illustrating body-weight changes in tumor bearing mice treated with the recombinant fusion protein of the disclosure and controls.

The tumor growth in response to different treatments is summarized in FIG. 10. Anti-HER3 mAb at 10 mg/kg showed significant anti-tumor activity with a tumor growth inhibition (TGI) of 93.5% at the end of study (p<0.001 vs. vehicle group). The recombinant fusion protein also demonstrated a statistically significant TGI at the end of the study: 19.2% at 1 mg/kg dosage (p=0.048 vs. vehicle group) and 56.2% at 10 mg/kg dosage (p<0.001 vs. vehicle group). The control molecule GP120 mAb/NRG-1 fusion protein showed no anti-tumor activity at either the high or low dose. No animal deaths occurred during the study. All test agents were well-tolerated by the tumor-bearing mice. There was no significant body-weight loss observed in any experimental group (FIG. 11). These data show that under the condition of active tumor growth in vivo, the recombinant fusion protein exhibits tumor growth inhibition in a dose-dependent manner, and suggests that the risk of the recombinant fusion protein augmenting or accelerating tumor growth in vivo is lower than the native NRG-1 protein.

Example 9—No Significant Gastrointestinal Toxicity Observed in Cynomolgus Monkeys Administrated with the Recombinant Fusion Protein It was previously reported that in a Phase One clinical study (NCT01258387) in which subjects received either placebo or single-dose administration of cimaglermin (full-length recombinant NRG-1β3), nausea and diarrhea were the second and fourth most common treatment-emergent adverse events, occurring in 40% and 27% of the aggregated high-dose cohorts respectively (Lenihan et al. J Am Coll Cardiol Basic Trans Science. 2016; 1(7):576-86). Similarly, in a Phase Two study of a recombinant NRG-1 peptide fragment (neucardin), nausea was the most commonly observed treatment-related adverse event, seen in 20% of the study subjects (Jabbour et al. European Journal of Heart Failure (2011) 13: 83-92). Finally, in a second Phase Two study of neucardin (ChiCTR-TRC-00000414), published results show 48.4% of the adverse events observed were gastrointestinal in nature, the most frequently observed type of adverse events in this study, and correlated with dose-level (Gao et al. J Am Coll Cardiol 2010; 55:1907-14).

Two studies to evaluate the safety and tolerability of the recombinant fusion protein in cynomolgus macaques (*Macaca fascicularis*) were conducted: a single-dose non-GLP (good laboratory practice) study and a repeat-dose GLP study. Gastrointestinal toxicities were closely monitored. In the single-dose study, the safety and tolerability of the recombinant fusion protein was evaluated at dose levels of 10, 30, and 60 mg/kg in comparison to vehicle control, with one male and one female animal included in each cohort. In this single-dose study there were no test agent-related effects on body weight or qualitative food evaluation throughout the post-treatment evaluation period of two weeks, and no observations of vomiting or diarrhea. In the repeat-dose GLP study, the safety and tolerability of the recombinant fusion protein was evaluated following four consecutive weekly administrations at dose levels of 3, 10, and 30 mg/kg in comparison to vehicle control, with three males and three females included in each cohort for the main 28-day study period, and an additional two males and two females in the 30 mg/kg and vehicle control cohorts evaluated following a subsequent 28-day recovery period. There were no test agent-related effects on food consumption observed in this repeat-dose study. While there was test agent-related vomiting observed in this repeat-dose study, clinical observations of vomiting were only associated with infusion reactions, only observed in one animal in the 10 mg/kg cohort (17%) and two animals in the 30 mg/kg cohort (20%), and were transient in nature. Diarrhea was observed only in the vehicle control cohort and 30 mg/kg recombinant fusion protein cohort, in only one (10%) and three (30%) animals respectively, and was considered normal for this type of procedure and unrelated to the recombinant fusion protein. Finally, in this repeat-dose study, average body weight was reduced by >10% relative to baseline only at the 10 mg/kg and 30 mg/kg dose levels, and only following the fourth dose in the 10 mg/kg cohort and the third and fourth doses in the 30 mg/kg cohort. In summary, treatment with the recombinant fusion protein did not result in any clinically significant findings related to food intake, vomiting, or diarrhea other than during acute infusion reactions, and gastrointestinal findings had no impact on the determination of the no-adverse event level in either study. These results indicate that the design of the recombinant fusion protein mitigates the adverse effect of NRG-1 recombinant protein on the gastrointestinal tract.

Figure 12:
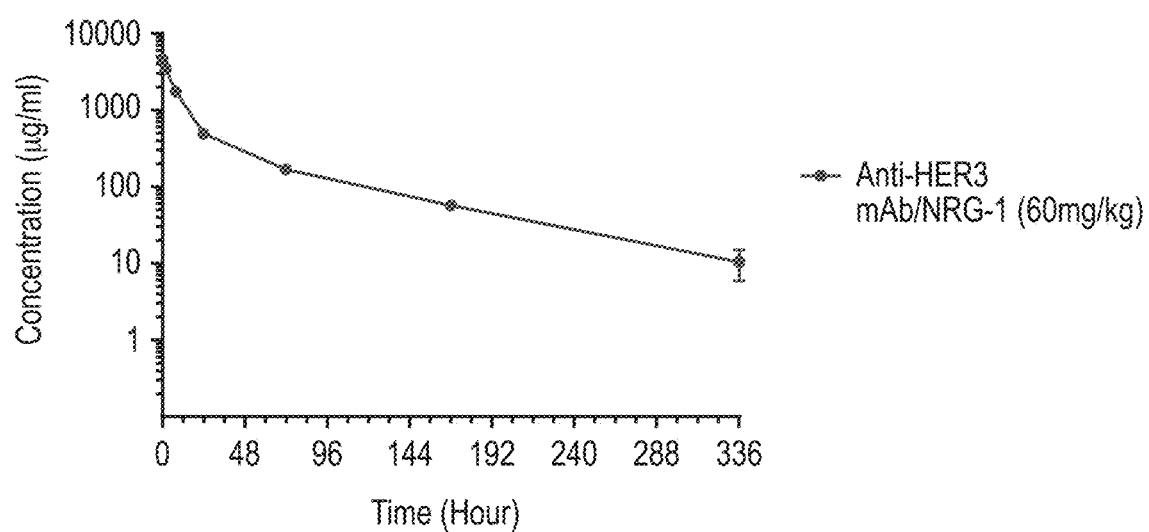
FIG. 12 is a graph illustrating the pharmacokinetic profile of the recombinant fusion protein in cynomolgus monkeys (macaques).

Blood samples (~1 ml) were collected from cynomolgus monkeys following single-dose administration of 60 mg/kg of the recombinant fusion protein at different time points, and sera were extracted and stored at −80° C. until tested. The concentrations of the recombinant fusion protein in the serum samples were assayed by capture ELISA according to standard procedures. Briefly, 96-well plates were coated with the recombinant human HER3 protein (R&D System), blocked with BSA, and incubated with test samples. After multiple washes, plates were incubated with HRP-conjugated anti-human IgG Fc antibody and then detected with TMB substrate. FIG. 12 shows that the pharmacokinetic profile of the recombinant fusion protein is similar to IgG antibody.

Example 10—Summary of Kinetic Constants on Fc Receptor Binding

The binding affinity between the recombinant anti-HER3 mAb/NRG-1 fusion protein and Fc receptors were measured using label-free SPR technique. A total of six Fc receptors (each fused with a His-tag), including FcγRI (Abcam), FcγRIIa, FcγRIIb, FcγRIIIa (158F), FcγRIIIa (158V), and C1q (Sino Biological), were analyzed against the recombinant fusion protein, the recombinant fusion protein without Fc mutations and anti-HER3 antibody, respectively. All Fc receptors and test samples were purified by affinity chromatography. All experiments were performed on Biacore 8K systems (GE Healthcare), with HBS-EP+ (10 mM HEPES, 150 mM NaCl, 3 mM EDTA and 0.05% v/v Surfactant P20) as the running buffer. Specifically, anti-His antibody was coupled in both the active and reference flow cell of a CM5 sensor chip by the amine coupling method. Purified His-tagged Fc receptors were captured on the active flow cell of each individual channel through binding to immobilized anti-His antibody. Capture level for each Fc receptor was maintained between 80-120 RU. For kinetic analysis, the recombinant fusion protein and all other samples were serially diluted to a total of 6 concentrations, ranging from 0.3 nM to 30 nM, and the serial dilutions were injected in sequence through both flow cells in each channel. Multiple analyses were completed in the same run by simultaneously injecting samples over multiple channels.

The resulting sensorgrams were fitted with a two-state binding model to extract kinetic constants using Biacore 8K Evaluation Software. Equilibrium dissociation rates (KD) of all analyses are summarized in Table 1 below. Kinetically derived KD values of the recombinant fusion protein binding to FcγRI, FcγRIIa and FcγRIIb, were more than 10-fold higher than those of the recombinant fusion protein without Fc mutations and the anti-HER3 antibody, indicating much lower affinities as a result of the specified mutations within the Fc region of the recombinant fusion protein. With FcγRIIIa (158F) and FcγRIIIa (158V), respectively, Fc mutations led to 2 to 3-fold reduction in binding affinity for the recombinant fusion protein. Binding to C1q was too weak to be detected for all samples.

To confirm that the recombinant fusion protein has limited Fc effector functions, antibody-dependent cellular cytotoxicity (ADCC) was examined using the ADCC Reporter Bioassay from Promega (Madison, Wis.). The assay used an engineered Jurkat cell line as effector cells, which stably expressed the FcγRIIIa (V158) receptor and an NFAT response element that drives the expression of firefly luciferase. Rituximab, as the positive control for the assay, showed strong ADCC activity against CD20-positive Raji cells; whereas the recombinant fusion protein had no detectable ADCC against HER3-positive target cells (MCF7 or BT474) (data not shown).

TABLE 1

Summary of kinetic constants on Fc receptors binding

| | KD (M) | | |
|---|---|---|---|
| Fc Receptors | Anti-HER3 mAb/NRG-1 | Anti-HER3 mAb/NRG-1 (w/o Fc mutations) | Anti-HER3 mAb |
| FcγRI | 1.03E−08 | 2.81E−09 | 4.56E−09 |
| FcγRIIa | 1.35E−06 | 3.95E−07 | 1.50E−07 |
| FcγRIIb | 1.52E−06 | 1.03E−07 | 1.04E−08 |
| FcγRIIIa (158F) | 1.18E−07 | 6.37E−08 | 1.66E−07 |
| FcγRIIIa (158V) | 9.10E−08 | 3.41E−08 | 3.80E−08 |
| C1q | <LOD* | <LOD* | <LOD* |

*<LOD - Below limit of detection (LOD) due to weak binding

What is claimed is:

1. A recombinant fusion protein comprising a fragment of the cardioprotective protein neuregulin-1 (NRG-1) fused to a monospecific ErbB3 (HER3) monoclonal antibody (mAb).

2. The recombinant fusion protein of claim 1, wherein the NRG-1 fragment comprises the ERBB3/4 binding domain.

3. The recombinant fusion protein of claim 1, wherein said NRG-1 fragment comprises the NRG-1 β2a isoform.

4. The recombinant fusion protein of claim 1, wherein the recombinant fusion protein comprises the amino acid sequences of SEQ ID NO: 3 and SEQ ID NO: 14.

5. The recombinant fusion protein of claim 1, wherein the recombinant fusion protein attenuates proliferation of tumor or cancer cells relative to recombinant NRG-1.

6. The recombinant fusion protein of claim 1, wherein the recombinant fusion protein promotes cardiomyocyte proliferation, differentiation, and survival.

7. The recombinant fusion protein of claim 1, wherein the recombinant fusion protein promotes proliferation, differentiation and survival of cardiac tissue.

8. The recombinant fusion protein of claim 1, wherein the recombinant fusion protein promotes proliferation, differentiation and survival of central nervous system (CNS) cells.

9. The recombinant fusion protein of claim 1, wherein the recombinant fusion protein has a reduced capacity to induce antibody-dependent cell cytotoxicity (ADCC).

10. The recombinant fusion protein of claim 1, wherein the recombinant fusion protein promotes HER2/4 signaling over HER2/3 signaling relative to the signal induction potential of recombinant NRG-1.

11. The recombinant fusion protein of claim 1, wherein the NRG-1 fragment comprises an active fragment.

12. The recombinant fusion protein of claim 11, wherein the active protein fragment of NRG-1 comprises the active domain of NRG-1.

13. The recombinant fusion protein of claim 1, wherein the NRG-1 fragment binds to and induces signaling through ErbB4 (HER4).

14. The recombinant fusion protein of claim 13, wherein the mAb inhibits NRG-1 signaling through ErbB3 (HER3).

15. The recombinant fusion protein of claim 1, wherein the NRG-1 fragment is fused via its N-terminal amino acid to the C-terminus of the antibody heavy chain using a linker.

16. The recombinant fusion protein of claim 15, wherein said linker comprises at least one copy of a Gly-Gly-Gly-Gly-Ser-Gly-Gly-Gly-Gly-Ser linker set forth in SEQ ID NO: 5.

17. The recombinant fusion protein of claim 15, wherein the C-terminus of the antibody heavy chain comprises the Fc domain of the antibody.

18. The recombinant fusion protein of claim 1, wherein the monoclonal antibody is glycosylated.

19. The recombinant fusion protein of claim 18, wherein the glycosylation is N-glycosylation.

20. The recombinant fusion protein of claim 18, wherein the glycosylation is O-glycosylation.

21. The recombinant fusion protein of claim 1 wherein the NRG-1 fragment comprises the amino acid sequence of SEQ ID NO: 4.

22. The recombinant fusion protein of claim 1, wherein the mAb comprises a heavy chain amino acid sequence of SEQ ID NO: 2.

23. The recombinant fusion protein of claim 22, wherein the mature mAb comprises a substitution mutation in at least one of amino acids 234, 239 and 434 of SEQ ID NO: 2.

24. The recombinant fusion protein of claim 23, wherein the at least one substitution mutation comprises a L234F mutation, a S239A mutation, a N434A mutation, or a combination thereof.

25. The recombinant fusion protein of claim 1, wherein the mAb comprises a light chain amino acid sequence of SEQ ID NO: 3.

26. A kit, comprising an effective amount of the recombinant protein of claim 1.

27. A pharmaceutical composition comprising the recombinant fusion protein of claim 1.

28. A method of inhibiting, suppressing or delaying the onset of a cardiovascular disease or condition in a subject, the method comprising administering an effective amount of the pharmaceutical composition of claim 27.

29. A method of treating a cardiovascular disease or condition in a subject in need thereof, the method comprising administering a therapeutically effective amount of the pharmaceutical composition of claim 27.

30. The method of claim 29, wherein the treatment alleviates a sign or a symptom of the cardiovascular disease or condition in the subject.

31. The method of claim 29, wherein the cardiovascular disease or condition is Chronic heart failure/Congestive heart failure (CHF), Acute heart failure/Myocardial infarction (MI), Left ventricular systolic dysfunction, Reperfusion injury associated with MI, Chemotherapy-induced cardiotoxicity (adult or pediatric), Radiation-induced cardiotoxicity, or Adjunct to surgical intervention in pediatric congenital heart disease.

32. The method of claim 31, wherein the chemotherapy-induced cardiotoxicity results from a subject receiving anthracyclines, alkylating agents, antimicrotubule agents, or antimetabolites agents used as chemotherapy.

33. The method of claim 29, wherein the cardiovascular condition is cardiotoxicity as a result of a subject receiving a cancer therapy.

34. The method of claim 33, wherein the cancer therapy is a HER-2 targeted therapy.

35. The method of claim 34, wherein the HER-2 targeted therapy comprises use of trastuzumab, ado-trastuzumab, emtansine, lapatinib, neratinib, pertuzumab, any anti-HER2 antibody, any anti-HER2 agent, or a combination thereof.

36. A recombinant nucleic acid molecule encoding the recombinant fusion protein of claim 1.

37. A recombinant vector comprising the nucleic acid molecule of claim 36.

38. A recombinant cell comprising the recombinant vector of claim 37.

* * * * *

SEQUENCE LISTING

<160> NUMBER OF SEQ ID NOS: 18

<210> SEQ ID NO 1
<211> LENGTH: 331
<212> TYPE: PRT

<213> ORGANISM: Homo sapiens

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 2
<211> LENGTH: 447
<212> TYPE: PRT
<213> ORGANISM: Homo sapiens

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr

```
                20                  25                  30
Tyr Trp Ser Trp Ile Arg Gln Pro Pro Gly Lys Gly Leu Glu Trp Ile
            35                  40                  45
Gly Glu Ile Asn His Ser Gly Ser Thr Asn Tyr Asn Pro Ser Leu Lys
        50                  55                  60
Ser Arg Val Thr Ile Ser Val Glu Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Asp Lys Trp Thr Trp Tyr Phe Asp Leu Trp Gly Arg Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
        210                 215                 220
Thr Cys Pro Pro Cys Pro Ala Pro Glu Phe Leu Gly Gly Pro Ala Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Ala His Tyr Thr Gln Lys Ser Leu Ser Leu Ser Pro Gly Lys
        435                 440                 445
```

```
<210> SEQ ID NO 3
<211> LENGTH: 220
<212> TYPE: PRT
<213> ORGANISM: Homo sapiens

<400> SEQUENCE: 3

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 4
<211> LENGTH: 61
<212> TYPE: PRT
<213> ORGANISM: Homo sapiens

<400> SEQUENCE: 4

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 5
<211> LENGTH: 10
<212> TYPE: PRT
<213> ORGANISM: Artificial
<220> FEATURE:
<223> OTHER INFORMATION: Glycine-Serine linker
```

<400> SEQUENCE: 5

Gly Gly Gly Gly Ser Gly Gly Gly Gly Ser
1               5                   10

<210> SEQ ID NO 6
<211> LENGTH: 1614
<212> TYPE: DNA
<213> ORGANISM: Homo sapiens

<400> SEQUENCE: 6

| | | | | | |
|---|---|---|---|---|---|
| atggagtttg | ggctgagctg | ggttttcctt | gttgctataa | taaaggtgt | ccagtgtcag | 60 |
| gtgcagctgc | agcagtgggg | agctggactg | ctgaagccaa | gcgagaccct | gtctctgaca | 120 |
| tgcgccgtgt | acggaggatc | cttcagcgga | tactattggt | cttggatcag | gcagccacct | 180 |
| ggcaagggac | tggagtggat | cggcgagatc | aaccactctg | ctccaccaa | ctacaatccc | 240 |
| tctctgaagt | cccgggtgac | catctccgtg | agacaagca | agaatcagtt | tccctgaag | 300 |
| ctgtccagcg | tgaccgccgc | tgacacagcc | gtgtactatt | gcgctaggga | caagtggacc | 360 |
| tggtatttcg | atctgtgggg | aaggggcacc | ctggtgacag | tgtcttccgc | tctacaaag | 420 |
| ggcccctccg | tgtttcctct | ggctccaagc | tctaagagca | cctctggagg | aacagccgct | 480 |
| ctgggatgtc | tggtgaagga | ttacttccct | gagccagtga | ccgtgagctg | gaactctggc | 540 |
| gccctgacct | ccggagtgca | tacatttccc | gctgtgctgc | agtccagcgg | cctgtatagc | 600 |
| ctgtcttccg | tggtgaccgt | gcctagctct | tccctgggca | cccagacata | catctgcaac | 660 |
| gtgaatcaca | agccctccaa | tacaaaggtg | gacaagagag | tggagcctaa | gagctgtgat | 720 |
| aagacccata | catgcccacc | atgtccagct | cctgagctgc | tgggaggacc | ttccgtgttc | 780 |
| ctgtttcctc | caaagccaaa | ggacaccctg | atgatctctc | gcaccctga | ggtgacatgc | 840 |
| gtggtggtgg | acgtgtccca | cgaggatcca | gaggtgaagt | tcaactggta | cgtggatggc | 900 |
| gtggaggtgc | ataatgctaa | gaccaagcct | agggaggagc | agtacaacag | cacctatcgg | 960 |
| gtggtgtctg | tgctgacagt | gctgcaccag | gactggctga | acggcaagga | gtacaagtgc | 1020 |
| aaggtgagca | ataaggccct | gccagctccc | atcgagaaga | ccatctctaa | ggccaagggc | 1080 |
| cagcccagag | agcctcaggt | gtatacactg | cccctagcc | gcgaggagat | gaccaagaac | 1140 |
| caggtgtctc | tgacatgtct | ggtgaagggc | ttctacccat | ctgacatcgc | tgtggagtgg | 1200 |
| gagtccaatg | gccagcccga | gaacaattat | aagaccacac | acccgtgct | ggactccgat | 1260 |
| ggcagcttct | ttctgtactc | caagctgacc | gtggataaga | gcaggtggca | gcagggcaac | 1320 |
| gtgttttcct | gcagcgtgat | gcacgaggcc | ctgcacaatc | attatacaca | gaaatctctg | 1380 |
| tccctgagcc | caggcaaggg | aggaggagga | agcggaggag | gaggcagctc | tcatctggtg | 1440 |
| aagtgtgctg | agaaggagaa | gaccttctgc | gtgaacggcg | gcgagtgttt | tatggtgaag | 1500 |
| gacctgtcta | atccatccag | atacctgtgc | aagtgtccca | acgagttcac | aggcgatcgc | 1560 |
| tgccagaatt | acgtgatggc | ctctttttat | aaggctgagg | agctgtacca | gtaa | 1614 |

<210> SEQ ID NO 7
<211> LENGTH: 1614
<212> TYPE: DNA
<213> ORGANISM: Homo sapiens

<400> SEQUENCE: 7

| | | | | | |
|---|---|---|---|---|---|
| atggagtttg | ggctgagctg | ggttttcctt | gttgctataa | taaaggtgt | ccagtgtcag | 60 |
| gtgcagctgc | agcagtgggg | agctggactg | ctgaagccaa | gcgagaccct | gtctctgaca | 120 |

```
tgcgccgtgt acggaggatc cttcagcgga tactattggt cttggatcag gcagccacct    180
ggcaagggac tggagtggat cggcgagatc aaccactctg gctccaccaa ctacaatccc    240
tctctgaagt cccgggtgac catctccgtg gagacaagca agaatcagtt ttccctgaag    300
ctgtccagcg tgaccgccgc tgacacagcc gtgtactatt gcgctaggga caagtggacc    360
tggtatttcg atctgtgggg aaggggcacc ctggtgacag tgtcttccgc tctctacaaag   420 ggcccctccg tgtttcctct ggctccaagc tctaagagca cctctggagg aacagccgct    480
ctgggatgtc tggtgaagga ttacttccct gagccagtga ccgtgagctg gaactctggc    540
gccctgacct ctggagtgca tacatttccc gctgtgctgc agtccagcgg cctgtatagc    600
ctgtcttccg tggtgaccgt gcctagctct tccctgggca cccagacata catctgcaac    660
gtgaatcaca gcccctccaa tacaaaggtg gacaagagag tggagcctaa gagctgtgat    720
aagacccata catgcccacc atgtccagct cctgagttcc tgggaggacc tgccgtgttc    780
ctgtttcctc caaagccaaa ggacacccty atgatctctc gcacccctga ggtgacatgc    840
gtggtggtgg acgtgtccca cgaggatcca gaggtgaagt tcaactggta cgtggatggc    900
gtggaggtgc ataatgctaa gaccaagcct agggaggagc agtacaacag cacctatcgg    960
gtggtgtctg tgctgacagt gctgcaccag gactggctga acggcaagga gtacaagtgc    1020
aaggtgagca ataaggccct gccagctccc atcgagaaga ccatctctaa ggccaagggc    1080
cagcccagag agcctcaggt gtatacactg cccctagcc gcgaggagat gaccaagaac    1140
caggtgtctc tgacctgtct ggtgaagggc ttctacccat ctgacatcgc tgtggagtgg    1200
gagtccaatg gccagcccga gaacaattat aagaccacac acccgtgct ggactccgat    1260 ggcagcttct ttctgtactc caagctgacc gtggataaga gcaggtggca gcagggcaac    1320
gtgttttcct gcagcgtgat gcacgaggcc ctgcacgctc attatacaca gaaatctctg    1380
tccctgagcc caggcaaggg aggaggagga agcggaggag gaggcagctc tcatctggtg    1440
aagtgtgctg agaaggagaa gaccttctgc gtgaacggcg cgagtgttt tatggtgaag    1500 gacctgtcta atccatccag atacctgtgc aagtgtccca acgagttcac aggcgatcgc    1560
tgccagaatt acgtgatggc ctcttttat aaggctgagg agctgtacca gtaa          1614

<210> SEQ ID NO 8
<211> LENGTH: 723
<212> TYPE: DNA
<213> ORGANISM: Homo sapiens

<400> SEQUENCE: 8
atggtgttgc agacccaggt cttcatttct ctgttgctct ggatctctgg tgcctacggg     60
gacatcgaga tgacccagtc tccagattcc ctggccgtga gcctgggaga gagggctaca   120
atcaactgcc ggtccagcca gtctgtgctg tactcttcca gcaacaggaa ttacctggcc   180
tggtatcagc agaatcccgg ccagcccct aagctgctga tctattgggc tagcaccaga   240
gagtctggag tgcctgaccg cttctctgga tccggaagcg gcacagactt caccctgaca   300
atctcttccc tgcaggccga ggacgtggcc gtgtactatt gccagcagta ttactctacc   360
cctaggacat cggccaggg caccaaggtg gagatcaagc ggacagtggc cgctccatcc   420
gtgttcatct ttccacccte cgacgagcag ctgaagtccg gaaccgctag cgtggtgtgc   480
ctgctgaaca cttctaccce aagagaggcc aaggtgcagt ggaaggtgga taacgctctg   540
cagagcggca attctcagga gtccgtgacc gagcaggaca gcaaggattc tacatattcc   600
ctgagctcta cccctgacact gtccaaggcc gattacgaga agcacaaggt gtatgcttgc   660
```

```
gaggtgaccc atcagggcct gtccagcccc gtgacaaaga gcttcaaccg cggcgagtgt    720
taa                                                                  723
```

<210> SEQ ID NO 9
<211> LENGTH: 537
<212> TYPE: PRT
<213> ORGANISM: Homo sapiens

<400> SEQUENCE: 9

```
Met Glu Phe Gly Leu Ser Trp Val Phe Leu Val Ala Ile Ile Lys Gly
1               5                   10                  15

Val Gln Cys Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
        115                 120                 125

Gly Thr Leu Val Thr Val Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350
```

```
Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys Gly Gly Gly Gly Ser Gly Gly Gly Gly Ser Ser His Leu Val
465                 470                 475                 480

Lys Cys Ala Glu Lys Glu Lys Thr Phe Cys Val Asn Gly Gly Glu Cys
                485                 490                 495

Phe Met Val Lys Asp Leu Ser Asn Pro Ser Arg Tyr Leu Cys Lys Cys
            500                 505                 510

Pro Asn Glu Phe Thr Gly Asp Arg Cys Gln Asn Tyr Val Met Ala Ser
        515                 520                 525

Phe Tyr Lys Ala Glu Glu Leu Tyr Gln
    530                 535

<210> SEQ ID NO 10
<211> LENGTH: 537
<212> TYPE: PRT
<213> ORGANISM: Homo sapiens

<400> SEQUENCE: 10

Met Glu Phe Gly Leu Ser Trp Val Phe Leu Val Ala Ile Ile Lys Gly
1               5                   10                  15

Val Gln Cys Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

Leu Gln Ser Ser Gly Leu Tyr Ser Leu Ser Ser Val Val Thr Val Pro
    195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Phe Leu Gly Gly
                245                 250                 255

Pro Ala Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
        435                 440                 445

Glu Ala Leu His Ala His Tyr Thr Gln Lys Ser Leu Ser Leu Ser Pro
    450                 455                 460

Gly Lys Gly Gly Gly Gly Ser Gly Gly Gly Gly Ser Ser His Leu Val
465                 470                 475                 480

Lys Cys Ala Glu Lys Glu Lys Thr Phe Cys Val Asn Gly Gly Glu Cys
                485                 490                 495

Phe Met Val Lys Asp Leu Ser Asn Pro Ser Arg Tyr Leu Cys Lys Cys
                500                 505                 510

Pro Asn Glu Phe Thr Gly Asp Arg Cys Gln Asn Tyr Val Met Ala Ser
            515                 520                 525

Phe Tyr Lys Ala Glu Glu Leu Tyr Gln
    530                 535

<210> SEQ ID NO 11
<211> LENGTH: 19
<212> TYPE: PRT
<213> ORGANISM: Homo sapiens

<400> SEQUENCE: 11

Met Glu Phe Gly Leu Ser Trp Val Phe Leu Val Ala Ile Ile Lys Gly
1               5                   10                  15

Val Gln Cys

<210> SEQ ID NO 12
<211> LENGTH: 240
<212> TYPE: PRT
<213> ORGANISM: Homo sapiens

<400> SEQUENCE: 12

```
Met Val Leu Gln Thr Gln Val Phe Ile Ser Leu Leu Leu Trp Ile Ser
1               5                   10                  15

Gly Ala Tyr Gly Asp Ile Glu Met Thr Gln Ser Pro Asp Ser Leu Ala
            20                  25                  30

Val Ser Leu Gly Glu Arg Ala Thr Ile Asn Cys Arg Ser Ser Gln Ser
        35                  40                  45

Val Leu Tyr Ser Ser Asn Arg Asn Tyr Leu Ala Trp Tyr Gln Gln
    50                  55                  60

Asn Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Arg Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 13
<211> LENGTH: 20
<212> TYPE: PRT
<213> ORGANISM: Homo sapiens

<400> SEQUENCE: 13

```
Met Val Leu Gln Thr Gln Val Phe Ile Ser Leu Leu Leu Trp Ile Ser
1               5                   10                  15

Gly Ala Tyr Gly
            20
```

<210> SEQ ID NO 14
<211> LENGTH: 518
<212> TYPE: PRT
<213> ORGANISM: Artificial
<220> FEATURE:
<223> OTHER INFORMATION: Heavy chain component of the recombinant fusion protein

<400> SEQUENCE: 14

-continued

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Val Thr Ile Ser Val Glu Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Asp Lys Trp Thr Trp Tyr Phe Asp Leu Trp Gly Arg Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
    210                 215                 220
Thr Cys Pro Pro Cys Pro Ala Pro Glu Phe Leu Gly Gly Pro Ala Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Val Leu Asp Ser
385                 390                 395                 400
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
```

```
                420             425             430
His Ala His Tyr Thr Gln Lys Ser Leu Ser Leu Ser Pro Gly Lys Gly
            435                 440                 445

Gly Gly Gly Ser Gly Gly Gly Ser Ser His Leu Val Lys Cys Ala
        450                 455                 460

Glu Lys Glu Lys Thr Phe Cys Val Asn Gly Gly Glu Cys Phe Met Val
465                 470                 475                 480

Lys Asp Leu Ser Asn Pro Ser Arg Tyr Leu Cys Lys Cys Pro Asn Glu
                485                 490                 495

Phe Thr Gly Asp Arg Cys Gln Asn Tyr Val Met Ala Ser Phe Tyr Lys
            500                 505                 510

Ala Glu Glu Leu Tyr Gln
        515

<210> SEQ ID NO 15
<211> LENGTH: 42
<212> TYPE: PRT
<213> ORGANISM: Homo sapiens

<400> SEQUENCE: 15

His Ala Arg Lys Cys Asn Glu Thr Ala Lys Ser Tyr Cys Val Asn Gly
1               5                   10                  15

Gly Val Cys Tyr Tyr Ile Glu Gly Ile Asn Gln Leu Ser Cys Lys Cys
            20                  25                  30

Pro Asn Gly Phe Phe Gly Gln Arg Cys Leu
        35                  40

<210> SEQ ID NO 16
<211> LENGTH: 44
<212> TYPE: PRT
<213> ORGANISM: Homo sapiens

<400> SEQUENCE: 16

His Phe Lys Pro Cys Arg Asp Lys Asp Leu Ala Tyr Cys Leu Asn Asp
1               5                   10                  15

Gly Glu Cys Phe Val Ile Glu Thr Leu Thr Gly Ser His Lys His Cys
            20                  25                  30

Arg Cys Lys Glu Gly Tyr Gln Gly Val Arg Cys Asp
        35                  40

<210> SEQ ID NO 17
<211> LENGTH: 42
<212> TYPE: PRT
<213> ORGANISM: Homo sapiens

<400> SEQUENCE: 17

His Glu Glu Pro Cys Gly Pro Ser His Lys Ser Phe Cys Leu Asn Gly
1               5                   10                  15

Gly Leu Cys Tyr Val Ile Pro Thr Ile Pro Ser Pro Phe Cys Arg Cys
            20                  25                  30

Val Glu Asn Tyr Thr Gly Ala Arg Cys Glu
        35                  40

<210> SEQ ID NO 18
<211> LENGTH: 22
<212> TYPE: PRT
<213> ORGANISM: Artificial Sequence
<220> FEATURE:
<223> OTHER INFORMATION: EGF like domain consensus sequence
```

-continued

```
<400> SEQUENCE: 18

Ala Glu Lys Glu Lys Thr Phe Cys Val Asn Gly Glu Cys Phe Met Val
1               5                   10                  15

Lys Asp Leu Ser Asn Pro
            20
```